(12) United States Patent
Ying et al.

(10) Patent No.: US 8,372,969 B2
(45) Date of Patent: *Feb. 12, 2013

(54) RNA INTERFERENCE METHODS USING DNA-RNA DUPLEX CONSTRUCTS

(75) Inventors: Shao-Yao Ying, San Marino, CA (US); Shi-Lung Lin, Arcadia, CA (US)

(73) Assignee: University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/911,654

(22) Filed: Oct. 25, 2010

(65) Prior Publication Data

US 2011/0098461 A1    Apr. 28, 2011

Related U.S. Application Data

(60) Division of application No. 11/871,004, filed on Oct. 11, 2007, now abandoned, which is a continuation-in-part of application No. 09/920,342, filed on Aug. 1, 2001, now Pat. No. 7,662,791.

(60) Provisional application No. 60/222,479, filed on Aug. 2, 2000.

(51) Int. Cl.
   *C07H 21/04* (2006.01)
(52) U.S. Cl. ............... 536/24.5; 536/24.31; 536/24.1; 514/44
(58) Field of Classification Search ................ None
   See application file for complete search history.

(56) References Cited

U.S. PATENT DOCUMENTS

| | | | |
|---|---|---|---|
| 4,289,850 A | 9/1981 | Robinson | 435/68 |
| 4,683,195 A | 7/1987 | Mullis et al. | 435/6 |
| 4,683,202 A | 7/1987 | Mullis | 435/91 |
| 4,945,082 A | 7/1990 | Carter | 514/44 |
| 4,950,652 A | 8/1990 | Carter | 514/44 |
| 4,965,188 A | 10/1990 | Mullis et al. | 435/6 |
| 5,075,216 A | 12/1991 | Innis et al. | 435/6 |
| 5,091,374 A | 2/1992 | Carter | 514/44 |
| 5,322,770 A | 6/1994 | Gelfand | 435/6 |
| 5,514,545 A | 5/1996 | Eberwine | 435/6 |
| 5,712,257 A | 1/1998 | Carter | 514/44 |
| 5,795,715 A | 8/1998 | Livache et al. | 435/6 |
| 5,817,465 A | 10/1998 | Mallet et al. | 436/6 |
| 5,888,779 A | 3/1999 | Kacian et al. | 435/91.2 |
| 5,906,980 A | 5/1999 | Carter | 514/44 |
| 6,130,040 A | 10/2000 | Lin | 435/6 |
| 6,159,714 A | 12/2000 | Usman et al. | 435/91.31 |
| 6,197,554 B1 | 3/2001 | Lin et al. | 435/91.1 |
| 6,218,142 B1 | 4/2001 | Wassenegger et al. | 435/69.1 |
| 2002/0114784 A1* | 8/2002 | Li et al. | 424/93.2 |
| 2002/0137709 A1* | 9/2002 | Lin et al. | 514/44 |
| 2003/0166282 A1* | 9/2003 | Brown et al. | 435/455 |
| 2004/0087526 A1 | 5/2004 | Lin et al. | |
| 2004/0259247 A1 | 12/2004 | Tuschl et al. | 435/375 |
| 2005/0287668 A1 | 12/2005 | Finney | |

OTHER PUBLICATIONS

Mohammad B. Bahramian, et al. "Transcriptional and Post-transcriptional Silencing of Rodent a1 (I) Collagen by a Homologous Transcriptionally Self-Silenced Transgene," Molecular and Cellular Biology, vol. 19, No. 1, 274-283 (Jan. 1999).

Jack R. Bateman, et al. "DNA Replication and Models for the Origin of piRNAs," BioEssays 29:382-385 Wiley Periodicals, Inc. (2007).

Guy J. Berchem, et al. "Androgens Induce Resistance to 6c/-2-mediated Apoptosis in LNCaP Prostate Cancer Cells," Cancer Research 55, 735-738 (Feb. 15, 1995).

Julia M. Bosher, et al. "RNA Interference: Genetic Wand and Genetic Watchdog," Nature Cell Biology, vol. 2, E31-E36, cellbio.nature. com, Macmillan Magazines Ltd. (Feb. 2000).

Cogoni, et al, "Gene Silencing in *Neurospora crassa* Requires a Protein Homologous to RNA-dependent RNA Polymerase," Nature (vol. 399) Macmillan Magazines Ltd. (May 13, 1999).

J. Compton, "Nucleic Acid Sequence-Based Amplification," Nature, vol. 350, 91-92 (Mar. 7, 1991).

Sayda M. Elbashir, et al. "Duplexes of 21-Nucleotide RNAs Mediate RNA Interference in Cultured Mammalian Cells," Nature, vol. 411, 494-498 (May 24, 2001).

M. J. Embleton, et al., "In-Cell PCR From mRNA : Amplifying and Linking the Rearranged Immunoglobulin Heavy and Light Chain V-genes Within Single Cells," Nucleic Acids Research, vol. 20, No. 15, 3831-3837 (1992) Oxford University Press.

Andrew Fire, et al., "Potent and Specific Genetic Interference by Double-stranded RNA in *Caenorhabditis elegans*," Nature, vol. 391, 806-810 (Feb. 19, 1998).

Sarah R. Grant, "Dissecting the Mechanisms of Posttranscriptional Gene Silencing: Divide and Conquer," Cell, vol. 96, 303-306 (Feb. 5, 1999) Cell Press.

Dirk Grimm, et al., "Fatality in Mice Due to Oversaturation of Cellular microRNA/short hairpin RNA pathways," Nature, vol. 441, 537-541 (May 2006).

Alia Grishok, et al., "Genetic Requirements for Inheritance of RNAi in *C. elegans*," Science, vol. 287, 2494-2497 (Mar. 31, 2000).

Rami N. Hannoush, et al., "Remarkable Stability of Hairpins Containing 2', 5'-Linked RNA Loops," J. Am. Chem. Soc, vol. 123, No. 49, 12368-12374 (2001).

D. L. Kacian, et al, "A Replicating RNA Molecule Suitable for a Detailed Analysis of Extracellular Evolution and Replication," Proc. Nat. Acad. Sci, USA, vol. 69, No. 10, 3038-3042 (Oct. 1972).

(Continued)

*Primary Examiner* — Kimberly Chong
(74) *Attorney, Agent, or Firm* — DLA Piper LLP (US)

(57) ABSTRACT

The present invention provides novel compositions and methods for suppressing the function or activity of a targeted gene through a novel intracellular piRNA-mediated RNAi mechanism, using RNA-DNA duplex constructs. The invention further provides novel methods and compositions for generating or producing RNA-DNA duplex agents, whose quantity is high enough to be used for the invention's gene silencing transfection and possibly in therapeutics applications. This improved RNA-polymerase chain reaction (RNA-PCR) method utilizes thermocycling steps of promoter-linked DNA or RNA template synthesis, in vitro transcription and then reverse transcription to bring up the amount of RNA-DNA duplexes up to two thousand folds within one round of the above procedure for using in D-RNAi-directed gene silencing.

13 Claims, 14 Drawing Sheets

OTHER PUBLICATIONS

Jason R. Kennerdell, et al., "Use of dsRNA-Mediated Genetic Interference to Demonstrate that *frizzled* and *frizzled 2* Act in the Wingless Pathway," Cell, vol. 95, 1017-1026 (Dec. 23, 1998) Cell Press.

Rene F. Ketting, et al., "*mut-7* of *C. elegans*, Required for Transposon Silencing and RNA Interference, Is a Homolog of Werner Syndrome Helicase and RNaseD," Cell, vol. 99, 133-141 (Oct. 15, 1999) Cell Press.

D. Y. Kwoh, et al., "Transcription-based Amplication System and Detection of Amplified Human Immunodeficiency Virus Type 1 with a Bead-Based Sandwich Hybridization Format," Proc. Natl. Acad. Sci, USA, vol. 86, 1173-1177 Biochemistry (Feb. 1989).

Kathryn A. O'Donnell, et al., "Mighty Piwis Defend the Germline Against Genome Intruders," Cell 129, 37-44 (Apr. 6, 2007) Elsevier Inc.

Shi-Lung Lin, et al., "In vivo Analysis of Cancerous gene expression by RNA-polymerase Chain Reaction," Nucleic Acids Research, vol. 27, No. 23, 4585-4589 (1999) Oxford University Press.

Shi-Lung Lin, et a)., "A Novel mRNA-cDNA Interference Phenomenon for Silencing bcl-2 Expression in Human LNCaP Cells," Biochemical and Biophysical Research Communications 281, 639-644 (2001).

Shi-Lung Lin, et al., "D-RNAi (Messenger RNA-antisense DNA Interference) as a Novel Defense System Against Cancer and Viral Infections," Current Cancer Drug Targets, vol. 1, No. 3, 241-247 (2001).

Shi-Lung Lin, et al., "Combinational Therapy for Potential HIV-1 Eradication and Vaccination," International Journal of Oncology 24, 81-88 (2004).

Shi-Lung Lin, et al., "Novel RNAi Therapy—Intron-Derived MicroRNA Drugs," Drug Design Reviews—Online, vol. 1, No. 3, 247-255 (2004).

David J. McConkey, et al., "Apoptosis Resistance Increases with metastatic Potential in Cells of the Human LNCaP Prostate Carcinoma Line," Cancer Research, 56, 55-94-5599 (Dec. 15, 1996).

Leonle Misquitta, et al., "Targeted Disruption of gene function in *Drosophila* by RNA interference (RNA-i): a roie for *nautilus* in embryonic somatic muscle formation," Proc. Natl. Acad. Sci USA, vol. 96, 1451-1456, Developmental Biology (Feb. 1999).

Manika Pat-Bhadra, et al., "Cosuppression of Nonhomologous Transgenes in *Drosophila* Involves Mutually Related Endogenous Sequences," Cell, vol. 99, 35-46 (Oct. 1, 1999) Cell Press.

Anthony J. Raffo, et al., "Overexpression of bcl-2 Protects Prostate Cancer Cells from Apoptosis in vitro and confers Resistance to Androgen Depletion in vivo," Cancer Research, 55 4438-4445 (Oct. 1, 1995).

Scott W. Knight, et al., "A Role for the RNase III Enzyme DCR-1 in RNA Interference and Germ Line Development in *Caenorhabditis elegans*," Science, vol. 293, 2269-2271 (Sep. 21, 2001).

Carol A. Sledz, et al., "Activation of the interferon System by Short-Interfering RNAs," Nature Cell Biology, vol. 5, No. 9, 834-839 (Sep. 2003).

Anne Smardon, et al., "EGO-1 Is Related to RNA-Directed RNA Polymerase and Functions in Germ-Line Development and RNA Interference in *C. elegans*," Current Biology, vol. 10, No. 4, 169-178 (Feb. 3, 2000).

George R. Stark, et al., "How Cells Respond to Interferons," Annu. Rev. Biochem. vol. 67 227-264 (1998).

Hiroaki Tabara, et al., The *rde-1* Gene, RNA Interference, and Transposon Silencing in *C. elegans* Cell, vol. 99, 123-132 (Oct. 15, 1999), Cell Press.

Anna Wargelius, et al., "Double-Stranded RNA Induces Specific Developmental Defects in Zebrafish Embryos," Biochemical and Biophysical Research Communications, vol. 263, 156-161 (1999).

Florence Wianny, et al., "Specific Interference with Gene Function by Double-Stranded RNA in Early Mouse Development," Nature Cell Biology, vol. 2, 70-75 (Feb. 2000).

Dun Yang, et al., "Evidence that Processed Small dsRNAs May Mediate Sequence-Specific mRNA Degradation During RNAi in *Drosophila* embryos," Current Biology, vol. 10, No. 19, 1191-1200 (Sep. 19, 2000).

Phillip D. Zamore, et al., "RNAi: Double-Stranded RNA Directs the ATP-Dependent Cleavage of mRNA at 21 to 23 Nucleotide Intervals," Cell, vol. 101, 25-33 (Mar. 31, 2000) Cell Press.

Chamberlin, et al. "New RNA Polymerase from *Eschehchia coli* infected with Bacteriophage T7," Nature vol. 228, (Oct. 17, 1970).

Colombei, et al., "Detection of the Apoptosis-Suppressing Oncoprotein *bcl-2* Hormone-Refractory Human Prostate Cancers," American Journal of Pathology, vol. 143, No. 8, (Aug. 1993).

Myers, et al., "Reverse Transcription and DNA Amplification by a *Thermus thennophilus* DNA Polymerase," Biochemistry, vol. 30, No. 31 (Aug. 6, 1991).

Sambrook, et al., "Molecular Cloning A Laboratory Manual" First & Second Editions, (1989).

Caplen NJ, "RNAi as a Gene Therapy Approach". Expert Opinion. Biol. Thera. (2003) vol. 3(4) 575-586. Achley Publications Ltd.

Paroo et al., "Challenges for RNAi in vivo" Trends in Biotechnology (2004), vol. 22(8) 390-394. Elsevier.

Novina et al."The RNAi Revolution" Nature 2004, vol. 430: 161-164. Nature Publishing Group.

Alexeev et al. Nature Biotech 2000, 18:43-47.

\* cited by examiner

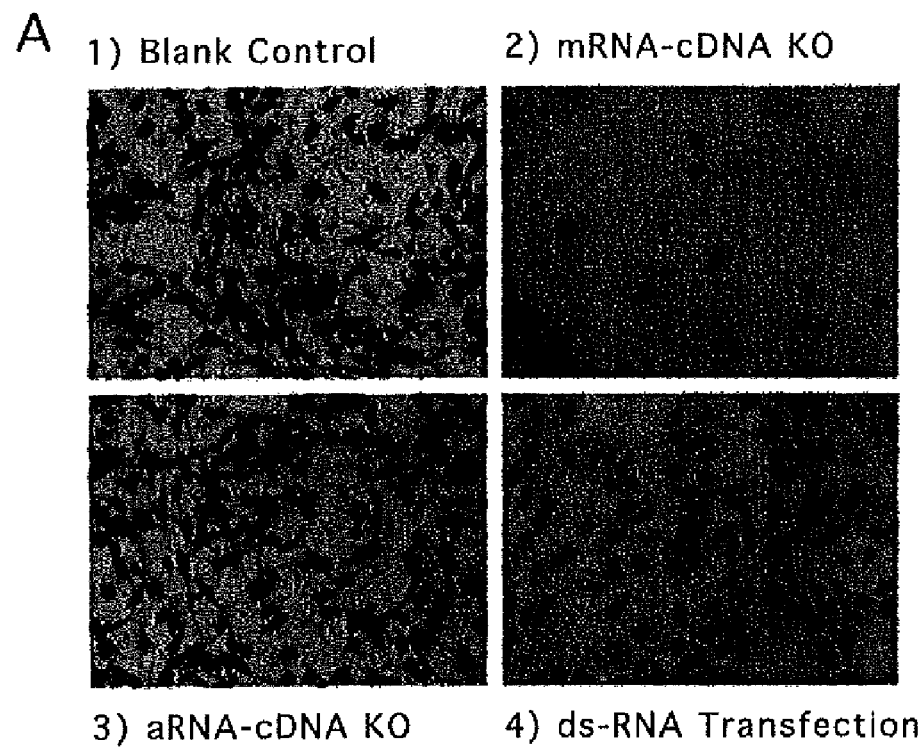
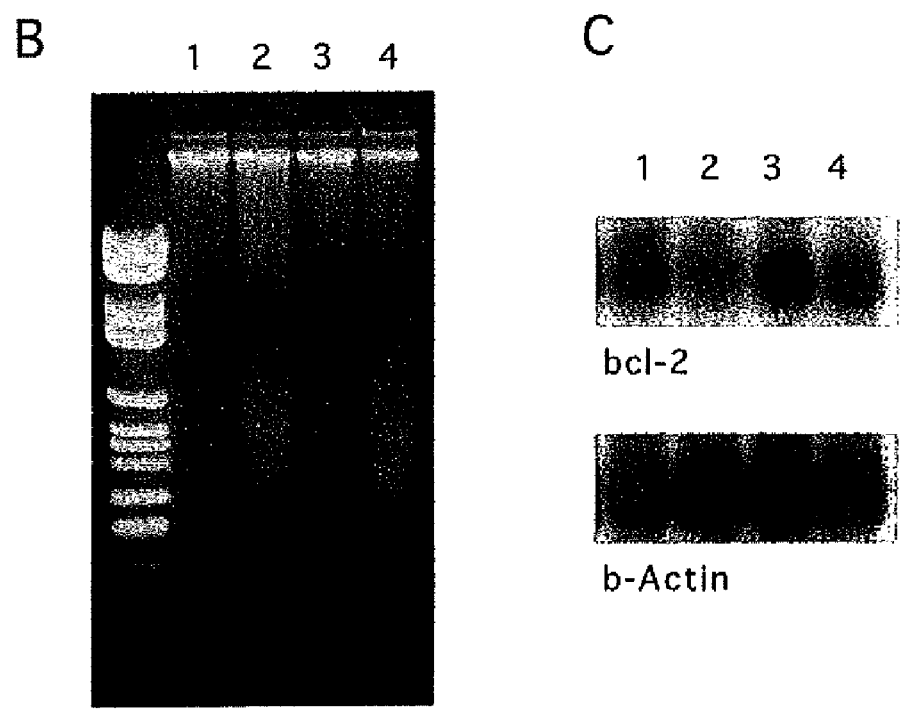
FIG. 3

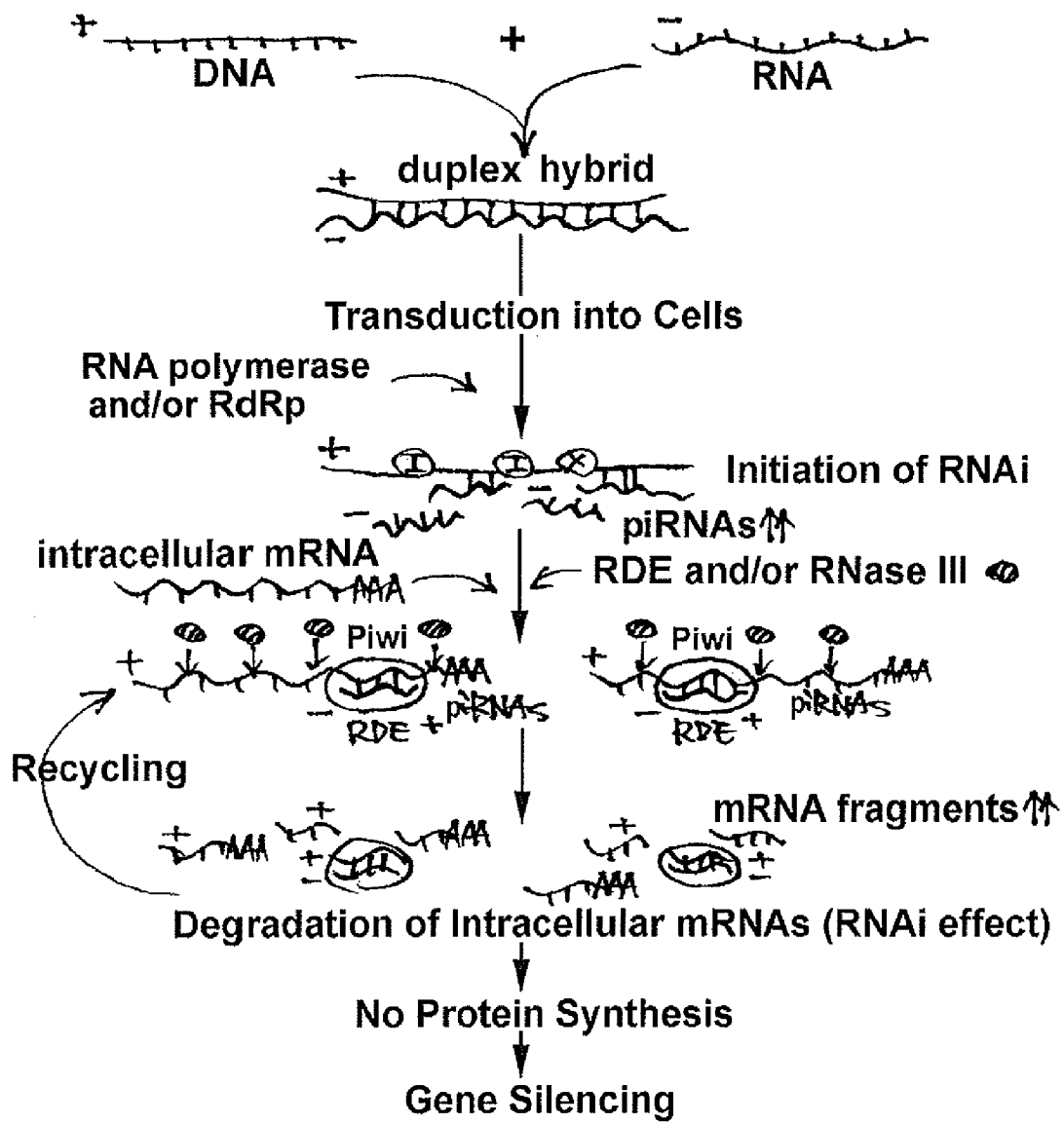

RNA INTERFERENCE METHODS USING DNA-RNA DUPLEX CONSTRUCTS

CLAIM OF THE PRIORITY

The present application is a divisional of application Ser. No. 11/871,004, filed on Oct. 11, 2007, which is a continuation-in-part patent application claiming priority to U.S. patent application Ser. No. 09/920,342 filed on Aug. 1, 2001, entitled "Gene Silencing Using mRNA-cDNA Hybrids", which is hereby incorporated by reference as if fully set forth herein. U.S. patent application Ser. No. 09/920,342 claims the benefit of U.S. Provisional application No. 60/222,479, filed Aug. 2, 2000.

GOVERNMENT FUNDING

This invention was made with support in part by a grant from the National Institute of Health (CA 85722). Therefore, the U.S. government has certain rights.

FIELD OF THE INVENTION

The present invention generally relates to the field of compositions and methods used in altering the genetic characteristics of eukaryotic cells through intracellular RNA interference (RNAi) mechanisms. In particular, it relates to suppression or inhibition of a specific gene function or transposon activity by means of DNA-RNA duplex-mediated mRNA degradation or genomic inactivation in eukaryotic cells.

Gene silencing, specific RNA molecule degradation or breakdown such as specific decay or suppression of the expression of gene transcripts, messenger RNAs (mRNA), hnRNAs, viral and other pathogenic RNAs, and other non-coding regulatory RNAs, holds great therapeutic and diagnostic promise. An example of this approach is the use of antisense oligonucleotides to inhibit gene expression in vitro and in vivo. Antisense technology involves the introduction into a cell of antisense oligonucleotide sequences that bind to target mRNA sequences in the cell with high affinity. This direct binding force degrades the mRNA and thus prevents mRNA translation. Many problems remain, however, with the effectiveness of the antisense technology. For example, single-stranded DNA antisense oligonucleotides exhibit relatively short-term effectiveness and are often toxic at the doses required for biological effectiveness. Similarly, single-stranded antisense RNAs are often quickly degraded due to their high secondary conformation and structural instability.

To overcome the merely binding force of the antisense technology, more advanced approaches were developed to inhibit or quell a specific target gene activity by means of the intracellular mechanisms of posttranscriptional gene silencing (PTGS) or RNA interference (RNAi). The PTGS/RNAi mechanisms have been applied to a variety of in-vivo systems, including plants, *Drosophila melanogaster*, *Caenorhabditis elegans*, and mouse. (Grant, S. R. (1999) *Cell* 96, 303-306; Kennerdell, J. R. and Carthew, R. M. (1998) *Cell* 95, 1017-1026; Misquitta, L. and Paterson, B. M. (1999) *Proc. Natl. Acad. Sci. USA* 96, 1451-1456; Pal-Bhadra, M., Bhadra, U., and Birchler, J. A. (1999) *Cell* 99, 35-46; Tabara, et al., (1999) *Cell* 99, 123-132; Ketting et al., (1999) *Cell* 99, 133-141; Fire et al., (1998) *Nature* 391, 806-811; and Grishok et al., (2000) *Science* 287, 2494-2497) as well as zebrafish (Wargelius et al., (1999) *Biochem. Biophys. Res. Commun.* 263, 156-161; Wianny, F. and Zernicka-Goetz, M. (2000) *Nature Cell Biol.* 2, 70-75). (These publications and all other cited publications and patents in this application are hereby incorporated by reference as if fully set forth herein.)

In general, the PTGS phenomena involve the transfection of a plasmid-like DNA or double-stranded DNA structure (transgene) into cells, while the RNAi phenomena involves the transfection of a double-stranded RNA (dsRNA) agent into the cells. These phenomena appear to evoke an intracellular sequence-specific RNA degradation process, affecting all highly homologous transcripts, called cosuppression. It has been proposed that such a cosuppression effect results from the generation of small interfering RNA (siRNA) products (about 21~25 base pairs in size) by RNA-directed RNA polymerases (RdRp) and/or endoribonucleases (RDE or RNaseIII Dicer) from an aberrant RNA template, derived from the transfection of nucleic acids or viral infection. (Grant S., supra; Ketting et al., supra; Bosher, J. M. and Labouesse, M. (2000) *Nature Cell Biology* 2, 31-36; Zamore et al., (2000) *Cell* 101, 25-33; and Elbashir et. al., (2001) *Nature* 411, 494-498).

Briefly, PTGS/RNAi involves the intracellular defense system of the cell, which directs RNA-dependent RNA polymerases (RdRp) and/or RNA-directed endoribonucleases (RDE or RNaseIII Dicer) to generate many double-stranded short interfering RNA fragments (siRNAs) from aberrant dsRNA templates. The siRNAs are further assembled in a RNA-induced silencing complex (RISC) along with the RDE or Dicer to execute the degradation or suppression of their targeted genes (Knight S W and Bass BL, (2001) *Science* 293, 2269-2271), resulting in RNAi-mediated gene silencing. Because the siRNA-associated RISC is highly sensitive to a double-stranded RNA construct, current RNAi methods prefer to use dsRNA (Fire, supra) as an aberrant template for triggering targeted gene silencing effects.

RdRp homologues have been widely found in *Arabidopsi thalianas* as Sde-1/Sgs-2, in *Neurospora crassa* as Qde-1; and in *Caenorhabditis elegans* as Ego-1; however, mammalian RdRp counterparts remain to be determined. Zamore et al., supra; Yang et al., (2000) *Current Biology* 10, 1191-1200; Cogoni, C. and Macino, G. (1999) *Nature* 399, 166-169; and Smardon et al., (2000) *Curr Biol.* 10, 169-171. In these biological systems, it seems that the RdRp activity appears to be a prerequisite for maintaining a long-term/inheritable PTGS/RNAi effect (Bosher et al. supra).

Although PTGS/RNAi phenomena appear to offer a potential avenue for inhibiting targeted gene expression, they have not been demonstrated to work well in higher vertebrates and, therefore, their widespread use in higher vertebrates in vivo is still questionable. For example, all currently found RNAi effects are based on the use of double-stranded RNA (dsRNA), which has been shown to cause interferon-induced non-specific RNA degradation (Stark et. al., (1998) *Annu. Rev. Biochem.* 67, 227-264; Elbashir et. al., (2001) *Nature* 411, 494-498; U.S. Pat. No. 4,289,850 to Robinson; and U.S. Pat. No. 6,159,714 to Lau). Such an interferon-induced cellular response often abolishes the specificity of RNAi-mediated gene silencing and causes cytotoxic effects to the treated cells. In mammalian cells, it has been noted that dsRNA-mediated RNAi phenomena are inhibited by the interferon-induced RNA degradation when the dsRNA size is larger than 30 base-pairs or its concentrations are more than 20 nM (Elbashir et al., supra; Sledz et al. (2003) *Nat Cell Biol.* 5, 834-839). The utilization of high-dose siRNAs (e.g., >250 nM in human T cells) also induces strong cytotoxicity similar to that of long dsRNA because high siRNA/shRNA concentrations can over-saturate the cellular microRNA pathway and thus causes global mRNA inhibition and cell death (Grimm et al., (2006) *Nature* 441, 537-541). For therapeutic use, these limitations exclude the possible utilization of dsRNA in vivo because it would be very difficult to maintain effective siRNA concentrations due to the high RNase and interferon activities of our bodies. Consequently, there remains a need for an effective and sustained method and composition for inhibiting gene function through the PTGS/RNAi-like cellular mechanisms.

SUMMARY OF THE INVENTION

The present invention provides a novel composition and method for inhibiting gene function and transposon activity in higher eukaryotes through a newly identified RNAi mechanism. Without being bound by any particular theory, this method is based on a RNA-DNA duplex-induced gene silencing phenomenon, potentially similar to, but slight different from, the PTGS/RNAi mechanisms, which is hereafter termed DNA-RNA interference (D-RNAi). In accordance with the present invention, DNA-RNA duplexes are used for inhibiting gene function and/or transposon activity. For example, both of the sense RNA (mRNA)-antisense DNA (cDNA) and the sense DNA (sDNA)-antisense RNA (aRNA) hybrid duplexes of the present invention have been shown to target a specific gene selected from the group consisting of pathogenic nucleic acids, viral genes, mutated genes, oncogenes and so on.

Recent studies have shown that the D-RNAi mechanism is resulted from the generation of Piwi-interacting RNAs (piRNA), which are distinct from other small double-stranded siRNAs and shRNAs by their relatively larger size (approximately 26-31 nucleotides), single-strandedness and strand-specificity as well as by the clustered arrangement of their origins (Bateman J R and Wu C T. (2007) *Bioessays* 29, 382-385). The piRNA class of small RNAs is likely transcribed by an intracellular RNA polymerase, similar to RdRp, from the DNA-RNA duplex region of a replicating cell genome during mitosis or meiosis. Mammalian type-II RNA polymerases have been observed to possess the RdRp activity (Shi-Lung Lin et al., (2001) *Biochem. Biophys. Res. Commun.* 281, 639-644). Nuclear transfection of DNA-RNA duplex templates has also been shown to trigger piRNA-like gene silencing effects against viral infection and jumping gene-like retrotransposon activity (Shi-Lung Lin et al. (2001) *Current Cancer Drug Targets* 1, 241-247; (2004) *Intrn'l J. Oncol.* 24: 81-88; and (2004) *Drug Design Reviews* 1: 247-255). In *Drosophila* and zebrafish, Piwi proteins are recently found to directly implicate in piRNA biogenesis to maintain transposon silencing in the germline genome (O'Donnell K A and Boeke J D. (2007) *Cell* 129, 37-44). This function may be conserved in mice as loss of Miwi2, a mouse Piwi homolog, leads to germline stem cell and meiotic defects correlated with increased transposon activity. Because the RNAi effector of the piRNA-mecliated gene silencing requires Piwi proteins rather than siRNA/shRNA-associated Dicer RNases, this suggests that the D-RNAi mechanism is slightly different from the siRNA/shRNA-mediated RNAi pathway.

Based on this newly identified piRNA-mecliated D-RNAi mechanism, the present invention relates to a novel gene-knockout or -knockdown method using the nuclear transfection of DNA-RNA duplex agents into the cells of interest, which can be a powerful new strategy in the fields of gene medicine and gene-modification technologies. The strength of this novel strategy is in its low dose, stability, safety and relatively long-term effectiveness. Applications of the present invention include, without limitation, the suppression of cancer progression by knocking out cancer-related oncogenes, the prevention and treatment of microbe infections by knocking out microbe-dependent genes, the study of candidate molecular signaling pathways with systematic knockout or knockdown of involved genes, and the high throughput screening of gene functions based on knocking out or down of a large number of targeted gene expression, possibly in conjunction with microarray or gene-chip analysis, etc. The present invention can also be used as a tool for studying gene function in various physiological conditions. The present invention provides a composition and method for altering the genetic characteristic of a eukaryotic cell through a novel RNAi-like mechanism.

In specific embodiments, the present invention provides a method for gene silencing, comprising the steps of: a) providing: i) a substrate expressing a targeted gene, and ii) a composition comprising a DNA-RNA duplex capable of silencing the expression of the targeted gene in the substrate; b) treating the substrate with the composition under conditions such that gene expression in the substrate is inhibited. The substrate can express the targeted gene in vitro or in vivo.

In one embodiment, the DNA-RNA duplex agent targets a gene selected from the group consisting of pathogenic nucleic acids, viral genes, mutated genes, and oncogenes. In another embodiment, differently constructed DNA-RNA hybrid duplexes inhibit β-catenin oncogene expression in vitro and in vivo, while the sense RNA (sRNA)-antisense DNA (cDNA) duplex inhibits bcl-2 expression in drug-resistant cancer cells. In yet another embodiment, both mRNA-cDNA (or termed sRNA-aDNA) and sDNA-aRNA duplexes suppress HIV-1 replication in CD4$^+$ T cells from primary cell culture in vitro as well as patients' samples ex vivo.

In another embodiment, the present invention provides RNA-DNA duplex compositions for altering the genetic characteristic of eukaryotic cells. In one aspect of the invention, the specific composition comprises a nucleic acid molecule that comprises a strand of deoxynucleic acid (DNA) molecule coupled to a strand of riboxynucleic acid (RNA) molecule. The RNA molecule is a sense RNA molecule that is homologous to a specific mRNA sequence to be targeted in the cell, while the DNA molecule is an antisense DNA molecule, which is complementary to the targeted mRNA, or vice versa. The RNA molecule also can be an antisense RNA molecule that is partially complementary to a specific messenger RNA (mRNA) sequence to be targeted in the cell, while the DNA molecule is a sense DNA molecule, which is in the same orientation and contains homologous sequence composition as the targeted mRNA. The use of an RNA-DNA duplex molecule is advantageous, among other reasons, because it does not trigger or otherwise has reduced occurrence of interferon-induced cytotoxicity, which is often seen in the use of double-stranded RNA (dsRNA) agents.

In yet another aspect of specific embodiments, the DNA and RNA strands of an RNA-DNA hybrid duplex can be synthesized by either enzymatic or chemical reactions. The synthesized RNA and DNA are usually generated in the 5' to 3' direction (3',5'-linkages) by polymerases; however, some chemical synthesizers do offer the 5' to 2' phosphodiester linkages (2',5'-linkages), with or without hexose-containing nucleotide analog(s). Both 2',5'-linked and 3',5'-linked RNAs share a highly similar chemical and biological property, so as to the 2',5'-linked and 3',5'-linked DNAs (Hannoush et. al., (2001) *J. Am. Chem, Soc.* 123, 12368-12374). The synthesized RNA strand containing deoxynucleotide-structured backbone and/or modified nucleotide analog(s) can function as a DNA or RNA strand of the RNA-DNA duplex molecule to protect the molecule from degradation and to increase knockout specificity. Therefore, the DNA and RNA strands of a DNA-RNA duplex agent may comprise at least one nucleotide analog such as inosine, xanthine, hypoxanthine, deoxyuracil, ribonucleotide, labeled nucleotide, 7-deaza-dNTP, methylthio-linked nucleotide, phosphothio-linked nucleotide, morpholino nucleotide, peptide nucleic acid (PNA), viral genome nucleic acid and so on. In another embodiment, the percent complementarity between the DNA and RNA strands of a DNA-RNA duplex agent can range from about 50% to 100%, with the preferred range between about 90% and about 100%. The RNA strand may be as long as the targeted mRNA molecule or may be shorter than the targeted mRNA molecule. The percent complementarity between the RNA strand and its targeted mRNA may range from about 70% to 100%, with the preferred range between about 90% to 100%. Furthermore, compositions comprising a plurality of the DNA-RNA duplex and articles of manufacture, such as kits and therapeutic, diagnostic, prognostic, and research reagents, comprising the DNA-RNA duplex agent or a plurality of the DNA-RNA duplex agents are also contemplated as part of the invention.

In another aspect of the invention, the introduction of the DNA-RNA duplex agent(s) into eukaryotic cell nucleus is useful and shown to alter the genetic characteristic of the eukaryotic cells. By nuclear transfection of the DNA-RNA duplex molecule, a novel natural cellular defense mechanism, similar to the RNAi phenomena, can be triggered and then interferes with the expression of its mRNA target(s), which shares high complementarity to the RNA strand of the DNA-RNA duplex agent. Some examples of the characteristics of the cell that may be altered include: expression of a cellular protein; cell viability, cellular metabolism, cell division; expression of a viral RNA and/or protein, replication of a pathogen genome, and any other cellular functions that contribute to the characteristics of the cell. Examples of cellular protein include proteins expressed from genes such as oncogenes, cell cycle related genes, signal transduction pathway related genes, and any other genes in the cell. Alteration of cellular characteristics may be useful for therapeutic applications such as reducing the proliferation of cancer cells, reducing viral or pathogenic infection by reducing the expression of vital pathogenic genes in the cell, and any other applications where interfering with the expression of the RNA and/or protein in the cell would have a beneficial and therapeutic effect. Alteration of cellular characteristics may also be useful in the study of a gene or its protein function, By interfering with the targeted gene expression, the specific gene function can be elucidated from the phenotypic change of the cell lacking the gene-coded protein product. Alteration of cellular characteristics may further be rendered by specific breakdown or degradation of non-gene-coding RNA and aberrant RNA molecules such as piRNA-targeted transposons, intronic RNAs, viral RNAs, and other genomic non-coding RNAs, which may possess known or unknown cellular function.

In another aspect of the invention, a method is provided for producing the DNA-RNA duplex molecule, which is capable of altering the genetic characteristic of a cell. Briefly, the method comprises the steps of synthesizing the RNA molecule, synthesizing the DNA molecule, and forming the DNA-RNA duplex molecule from the RNA and DNA molecule. The RNA may be synthesized chemically, or through in vitro transcription from a double- or single-stranded nucleic acid template having a RNA polymerase promoter sequence or replicase recognition site. The DNA molecule may be synthesized chemically, by polymerase chain reaction (PCR), or through reverse transcription from an RNA molecule. The DNA-RNA duplex molecule may also be formed by repeated steps of in vitro transcription IVT) and reverse transcription (RT) reactions.

BRIEF DESCRIPTION OF THE DRAWINGS

Referring particularly to the drawings for the purpose of illustration only and not limitation, there is illustrated:

FIG. 3 shows the use of different RNA-DNA duplex templates for bcl-2 gene interference, according to one embodiment of the present invention.

FIG. 9A shows an embryonic liver prior to nuclear microinjection; FIG. 9B shows the liver after the injection of the RNA-DNA duplexes. Blue dye indicates the success of nuclear transfection. FIG. 9C shows the Northern blotting results of β-catenin gene silencing after treatment with the RNA-DNA duplexes, while FIG. 9D shows no off-target effect on a control gene GAPDH. Lanes 1-3 are samples transfected by the RNA-DNA duplexes, whereas lanes 4-6 show the liposomal control samples without the treatment.

FIG. 11 is a general illustration of the preferred embodiment of DNA-RNA duplex-mediated RNAi gene silencing of the subject invention.

DETAILED DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Gene Silencing Using RNA-DNA Duplexes

In Vitro Prostate Cancer Model

As noted earlier, posttranscriptional gene silencing (PTGS) and RNA interference (RNAi) have been found capable of quelling specific gene activities in a variety of in vivo systems.

According to the invention provided herein, ectopic transfection of a sequence-specific RNA-DNA duplex (instead of a transgene or dsRNA) is used to induce intracellular gene silencing in human cells. Although previous transgene/dsRNA transfection experiments showed that PTGS/RNAi effects are limited to plants and some simple animals, using the present invention, specific gene interference of bcl-2 expression in human LNCaP prostate cancer cells using the long RNA-DNA duplex has been successfully detected.

Normal human prostatic secretory epithelial cells do not express bcl-2 protein, whereas neoplastic prostate tissues from androgen-ablation patients show an elevated level of this apoptosis-suppressing oncoprotein. It is known in the art that over-expression of bcl-2 protects prostate cancer cells from apoptosis in vitro, and confers resistance to androgen depletion in vivo. The tumorigenic and metastatic potentials of LNCaP cells are also significantly increased after bcl-2 stimulation by either androgen or transgene treatment. Such inhibition of apoptosis can be blocked by treatment with bcl-2 antisense oligonucleotides, but many apoptotic stimuli such as etoposide or phorbol ester cannot be blocked.

Figure 2:
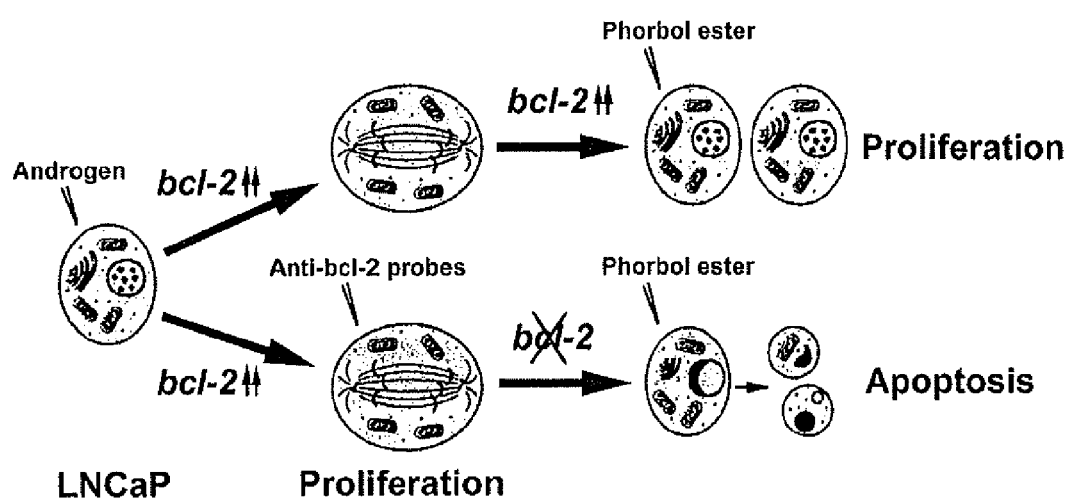
FIG. 2 shows a schematic representation of experimental procedures for testing RNA interference of bcl-2 gene expression in androgen-treated human prostate cancer LNCaP cells, according to one embodiment of the present invention.

The potential utility of RNA-DNA duplexes in preventing bcl-2 expression was therefore tested on androgen-stimulated LNCaP cells, expecting to increase cancer cell susceptibility to apoptotic stimuli and reduce tumorigenic outgrowth in vitro. Following previous findings, LNCaP cells were treated with dihydrotestersterone (100 nM 5□-anrostan-17□-01-3-one) to block the apoptotic effect of phorbol ester (10 nM phorbol-12-myristate-13-acetate). When treated with the methods and compositions of this invention LNCaP cells induced a bcl-2 knockdown effect to resume the apoptosis of the androgen- and phorbol ester-treated cancer cells (FIG. 2).

FIG. 3 shows the analysis of different templates for bcl-2 gene interference, namely: (1) blank control; (2) mRNA-cDNA duplex (the same as sRNA-aDNA hybrid); (3) perfectly matched aRNA-cDNA hybrid; and (4) dsRNA in LNCaP cells. FIG. 3A shows changes of cell proliferation rate and morphology. Chromosomal DNAs were stained by propidium iodide. Although the dsRNA transfection also showed minor morphological changes, a significant cell growth inhibition and chromosomal condensation only occurred in the mRNA-cDNA transfection (n=4). FIG. 3B shows genomic laddering patterns demonstrating apoptosis induction by the bcl-2 mRNA-cDNA transfection. FIG. 3C presents the Northern blot results showing a strong gene silencing effect induced by the mRNA-cDNA transfection against the targeted bcl-2 expression. As shown in FIG. 3, the transfection of bcl-2 mRNA-cDNA duplexes (5 nM) into LNCaP cells was sufficient to silence bcl-2 expression and caused apoptosis in these cancer cells (e.g. chromosomal condensation and genomic DNA laddering fragmentation).

There are three major effects of PTGS, i.e., initiation, spreading and maintenance, all of which are also found in many inheritable RNAi phenomena. The initiation indicates that the onset of PTGS/RNAi takes a relatively long period of time (1-3 days) to develop enough small RNAs or short aRNAs for specific gene knockout. With the antisense transfection processes, it only takes several hours to reach the same gene silencing results but with much higher dosages and higher cytotoxicity. Also, unlike the short-term effectiveness of traditional antisense transfections, the PTGS/RNAi effects may spread from a transfected cell to neighboring cells and can be maintained for a very long time (weeks to lifetime) in a mother cell as well as its daughter cells.

Figure 4:
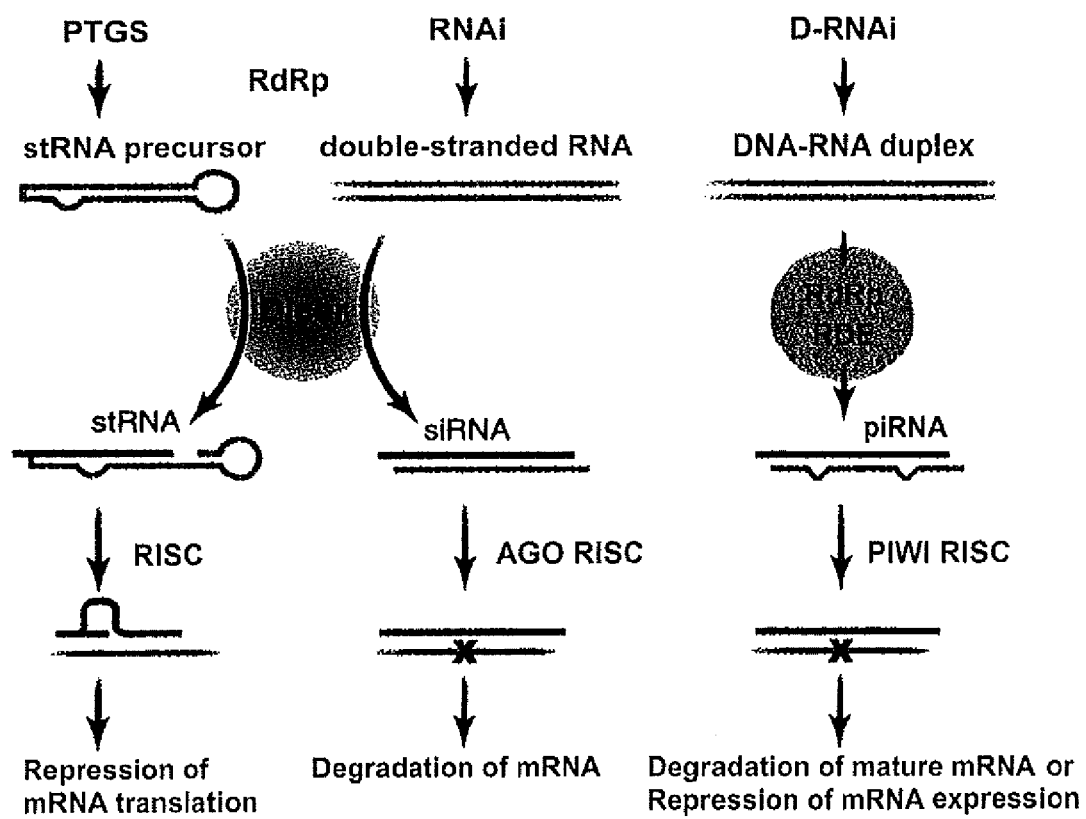
FIG. 4 shows a comparison among the long-term PTGS, siRNA-mediated RNAi and piRNA-mediated D-RNAi mechanisms.
Figure 5:
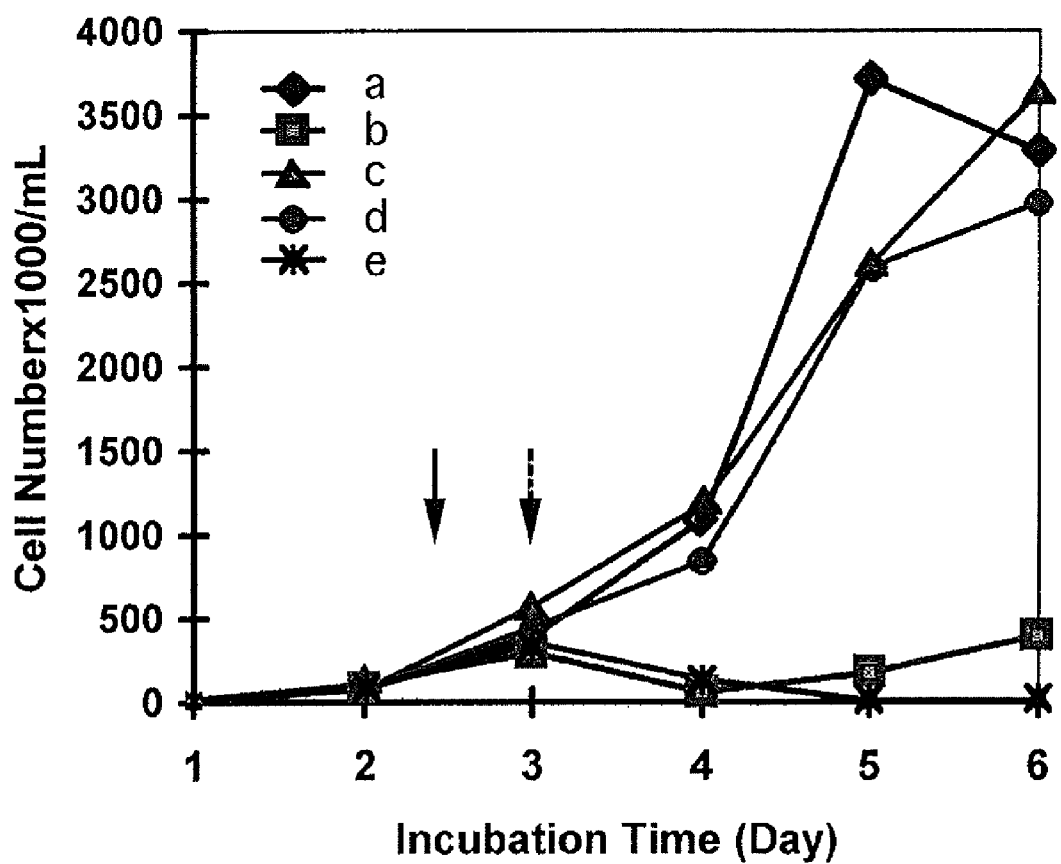
FIG. 5 shows a linear plot of the interaction between incubation time and cell growth number in the methods of the present invention.

The results of the experiments here suggest that the invention shares some features of the PTGS/RNAi mechanisms. FIG. 4 shows a comparative model for long-term PTGS, siRNA-associated RNAi and piRNA-mediated D-RNAi mechanisms. Initiation and maintenance periods are varied, depending on different living systems and transfected genes. Because liposomal transfection methods offer only a 30~40% transfection rate per treatment, a complete apoptosis induction in the LNCaP cell model used required at least two to three transfections (FIG. 5). FIG. 5 shows a linear plot of the interaction between incubation time (X) and cell growth number (Y), indicating no spreading effect of the PTGS mechanism. The black linear arrow shows the first addition of all tested probes, while the dotted arrow indicates the second addition of an mRNA-cDNA probe for double transfection analysis. The growth of mRNA-cDNA (red and black) transfected cells remarkably inhibited after 36-hour incubation (n=4). Because one transfection is not sufficient to reach the entire cell population, a more complete inhibition of cell growth is achieved after double transfections (black), indicating no spreading effects.

Identification of A Potential RdRp-Like Enzyme For Gene Silencing In LNCaP Cells RNA polymerase II has been found to possess RNA-directed RNA synthesis activity (Filipovska et al., RNA 6: 41054 (2000); Modahl et al., *Mol. Cell Biol.* 20: 6030-6039 (2000)). Furthermore, the addition of low-dose α-amanitin (1.5 μg/ml), an RNA polymerase II-specific inhibitor derived from a mushroom *Amanita phalloides* toxin, abrogated the apoptosis induction of bcl-2 D-RNAi (FIG. 6).

Figure 6:
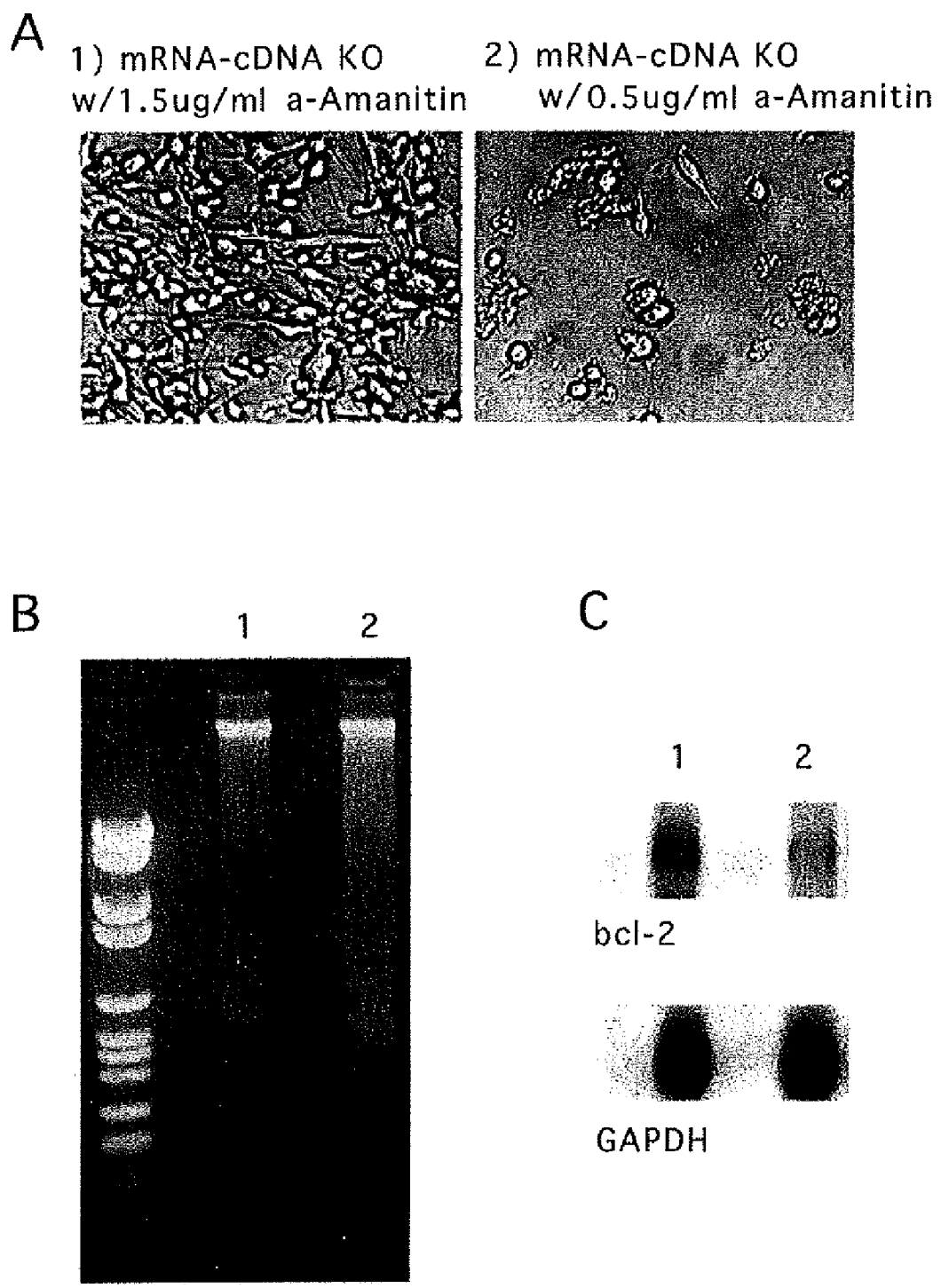
FIG. 6 shows a potential D-RNAi-associated RdRp enzyme with high α-amanitin sensitivity.

FIG. 6 shows an analysis of a potential RdRp enzyme by different α-amanitin sensitivity: (1) 1.5 μg/ml and (2) 0.5 μg/ml. FIG. 6A shows the changes of cell proliferation rate and morphology after addition of α-amanitin. A significant reduction of apoptosis was detected in the 1.5 μg/ml α-amanitin addition (but not in the 0.5 μg/ml α-amanitin addition) after mRNA-cDNA (equal to sRNA-aDNA) transfection (n=3), showing a dose-dependent release of cell growth inhibition. FIG. 6B shows genomic laddering patterns demonstrating the blocking of the apoptotic induction effect of the bcl-2 mRNA-cDNA transfection by the 1.5 μg/ml α-amanitin addition. FIG. 6C shows Northern blots indicating that the bcl-2 silencing effect was prevented.

Gene Silencing Using RNA-DNA Duplexes

An In Vivo Model Targeting β-catenin In Developing Chicken Embryos

As shown in the form of mRNA-cDNA duplex above, the foregoing establishes that the novel sRNA-aDNA duplexes of the present invention can be used in a novel strategy to knock out targeted gene expression in vitro. As discussed below, the novel sRNA-aDNA strategy of the invention is also effective in knocking out gene expression in vivo.

As illustrated in the examples below, the methods and compositions of the invention are effective in knocking out targeted gene expression in vivo in a developing chicken embryo. For molecules, β-catenin was targeted because it has a critical role in development and oncogenesis, and for tissue, skin and liver were selected because the skin is accessible and the liver is an important organ. β-catenin is known to be involved in the regulation of growth control. It has been suggested that β-catenin is involved in neovasculogenesis and that it may work with VE-cadherin, which is not essential for the initial endothelial adhesion but is required in further vascular morphogenesis to properly form mature endothelial walls and blood vessels.

As discussed above, the experimental results establish that sRNA-aDNA (as shown in mRNA-cDNA) duplexes potently inhibit β-catenin expression in the liver and skin of developing chick embryos. Thus, the results show that using a sRNA-aDNA duplex provides a powerful new strategy for gene silencing. A perfect matched sDNA-aRNA duplex usually does not appear to work well even though dominant-negatively transfected aRNA has been previously shown to suppress gene expression. This may be due to the strong affinity of the perfectly matched sDNA-aRNA hybrid, which exclude the engagement of RdRp activity needed for the small piRNA generation. The results also show that this invention is effective in knocking out the targeted gene expression over a long period of time (>10 days). Further, it was observed that non-targeted organs appear to be normal, which implies that the compositions herein possess no overt toxicity. Thus, the invention offers the advantages of low dosage, stability, long-term effectiveness, and lack of overt toxicity.

By disrupting the strong complementarity of a DNA-RNA duplex, the present invention also provides a novel composition and method for altering a characteristic of a cell. Without being bound by any particular theory, the alteration of a characteristic of the cell may be based on an RNAi-like gene silencing phenomenon, triggered by the introduction of a DNA-RNA duplex molecule into the cell. Generally, as seen in FIG. 11, when the DNA-RNA duplex molecule is transduced, transfected, or otherwise introduced into the cell(s) of interest, small piRNA fragments (25-30 nucleotides) may be produced by intracellular RdRp and then cleaved or disassociated from the DNA strand by RDE processing. The small piRNA are further assembled into a Piwi-dependent RNA-induced silencing complex (RISC), which is the key effector of the D-RNAi gene silencing mechanism capable of hybridizing to their target mRNA or transposon for degradation or inactivation.

Some of the advantages of the DNA-RNA duplex molecule over dsRNA transfection are listed as follows: 1) the DNA portion of a DNA-RNA duplex can be modified to stabilize the efficacy of RNAi phenomenon induction; 2) the RNA portion of a DNA-RNA duplex is well protected by the DNA portion of the same for more stable transfection (Lin (2001) supra); 3) the RNAi-associated RNA-directed endoribonucleases (RDE) have experimentally been shown to possess high activity to the RNA portion of a DNA-RNA duplex (see FIG. 12B; 4) the DNA-RNA duplex construct has been tested to suppress the interferon-induced cytotoxicity which is usually caused by dsRNA (see FIG. 13B and Example 13); and 5) the size of a DNA-RNA duplex can be larger than 30 base pairs for more effective transfection and specific gene targeting.

As seen in FIG. 11, the RNA of the DNA-RNA molecule is a RNA complementary to the targeted messenger RNA (mRNA) in the cell. The RNA is coupled to a DNA which is homologous to the sequence of the targeted mRNA in the cell. The complementation between the DNA molecule and the RNA molecule of the DNA-RNA duplex may range from about 20% to 100%, with the preferred range between about 45% to about 99%, most preferably about 95% in a linearly complementary form or about 48% in a palindromic form sequence. One way of introducing mismatch and therefore reduce the affinity of the DNA molecule and the RNA molecule is to treat the duplex with enzymes or chemicals that will generate nucleotide analogs in the DNA strand of the DNA-RNA hybrid duplex. For example, the nucleotide analogs can be generated by adding deaminase or acidic chemicals to the DNA portion of the DNA-RNA hybrid duplex, resulting in analogs such as of inosine (I), xanthine (x), hypoxanthine (HX), uracil (U), DNA-linked ribonucleotides and their derivative analogs (See e.g., U.S. Pat. No. 6,130,040, which is hereby incorporated by reference). Other methods of generating deoxynucleotide analogs include direct incorporation of analogs (inosine xanthine (x), hypoxanthine (HX), deoxyuracil (dU), ribonucleotide in a DNA linkage, deoxyribonucleotide in an RNA linkage, 7-deaza-dNTP, labeled nucleotides, and their derivative analogs, such as hexose-containing, 2'-5' linked, phosphothio-linked, methylthio-linked, morpholino-linked and peptide-linked nucleotide analogs) during the synthesis of the DNA and/or RNA. The DNA can be synthesized chemically by using an oligonucleotide synthesizer or through in vitro enzymatic reactions such as PCR, reverse transcription, DNA polymerase extension reaction wherein the deoxynucleotide and deoxynucleotide analogs are present in the reaction.

In accordance with one aspect of the present invention, DNA-RNA duplexes are used for inhibiting gene function. For example, the DNA-RNA duplex-mediated gene knockout or gene silencing technology can be used as a powerful new strategy in the field of gene-based therapy. As seen in the examples discussed below, the advantages of this novel strategy are in its low dose, stability, and potential long-term effects. The DNA-RNA duplexes of the present invention can be used to target a gene such as functional genes, pathogenic nucleic acids, viral genes/genomes, bacterial genes, mutated genes, oncogenes and any other genes functionally expressing RNA or protein. Examples of oncogenes are β-catenin, bcl-2, c-myc, etc. Examples of functional genes include tyrosinase, p53, TNF-α, etc. Examples of virus, the genes of which can be targeted, include HIV, HCV, Rhinovirus, Herpes virus, Papilloma virus, CMV, Ebola, and any other pathogenic or oncogenic viruses.

Although the preferred target for RNAi is the mRNA in the cell, not all targeted RNA for RNAi degradation are required to be capable of expressing a protein. Other types of RNA such as tRNA, rRNA, present naturally in the cells may also be targeted if desired. Furthermore, non-protein expressing portion of RNA viruses, for example, which replicate in eukaryotic cells may also be targeted for degradation, thereby reducing the ability of the virus to replicate.

The inhibition of gene expression by using the DNA-RNA duplex agent may also be applied to study the gene function of unknown nucleic acid transcripts. For example, the DNA-RNA duplex molecule can be introduced to a cell expressing a target gene transcript or mRNA with an unknown function. The inhibitory effect of this kind of targeted gene silencing may then alter the characteristic of the cell, which will provide clues as to the possible function of the gene. Candidate genes for this approach can be identified by comparison of the differentially expressed genes in two different types of cells (e.g., cancerous cells vs. non-cancerous cells; muscle vs. brain) or at different stages of cell cycle or animal development. The identification of differential gene expression may be achieved using subtractive hybridization, differential display, array or microarray technologies, and any other techniques used for comparing the gene expression in two different cells or cell conditions.

To increase the onset of RNAi-related effects in cells, the DNA portion of a DNA-RNA duplex can be modified to increase the efficiency of release of the RNA portion to an RNAi-associated RNA-directed endoribonuclease (RDE). Such modification can be accomplished either by the incorporation of weak binding nucleotide analogs during the synthesis of the DNA portion or the mild deamination of the DNA sequence nucleotides after its synthesis. For the incorporation method, the nucleotide analogs are integrated into the DNA sequence using an oligonucleotide synthesizer machine (e.g. SEQ ID.19) or an enzymatic reaction, such as reverse transcription (RT), polymerase chain reaction (PCR), nucleic acid sequence based amplification (NASBA) and RNA-polymerase cycling reaction (RNA-PCR (e.g. Example 12). The nucleotide analog can be selected from the group consisting of ribonucleotide in DNA linkage, deoxyuracil (dU), inosine (I), xanthine(X), hypoxanthine (HX) and their derivative analogs, such as hexose-containing, 2'-5' linked, phosphothio-linked, methylthio-linked, morpholino-linked and peptide-linked nucleotide analogs. Alternatively, the nucleotide analog can be generated by adding deaminase or acidic chemicals (e.g. acetic acid) to the DNA sequence, resulting in derivative analog(s) selected from the group consisting of inosine (I) and its derivatives (See e.g., U.S. Pat. No. 6,130,040).

Furthermore, the percent complementation between the DNA molecule and the RNA molecule in the DNA-RNA duplex may be adjusted, resulting in stronger or weaker hybridization between the two strands. The percent complementation may range from about 20% to 100%, whereby the percent complementation is determined by the ratio of the mismatching bases between the DNA molecule and the RNA molecule and the number of total bases (matched+mismatched) in one strand of the molecule (DNA or RNA). For example, if a particular DNA-RNA duplex molecule has the particular sequence as shown below, the percent complementation is 75% (1 mismatch GIU to 4 total bases):

DNA GGCG
RNA CUGC

Preferably, the percent complementation between the DNA and the RNA molecule in the DNA-RNA duplex molecule is between about 50% to about 90%.

The length of the DNA-RNA duplex molecule can also be controlled and adjusted if desired. Unlike dsRNA, the DNA-RNA duplex molecule does not trigger interferon-induced cytotoxicity in the targeted cells, Thus, the DNA-RNA duplex may range from as small as 15 basepairs to 2 kilobasepairs, preferably ranging from 25 basepairs to 500 basepairs.

Method of Generating the DNA-RNA Duplexes

The DNA-RNA duplex may be generated in a number of different ways. The DNA and the RNA may, for example, be separately synthesized by chemical synthesis using an oligonucleotide synthesizer. After synthesis, the DNA and the RNA strands may then be combined together by allowing them to anneal to each other. Alternatively, the DNA may also be synthesized from the chemically synthesized. RNA using a reverse transcriptase enzyme, primers complementary to the RNA, and deoxynucleotides in a reverse transcription reaction.

The RNA may also be synthesized through in vitro transcription of the RNA from a double stranded DNA that has an RNA polymerase sequence such as T7, SP6 or T3 RNA polymerase promoter. The double stranded DNA may be a plasmid, or a linear piece of DNA generated by PCR or restriction digest. After the in vitro transcription reaction, the resulting RNA may then be the source of template for a reverse transcriptase reaction to generate DNA-RNA duplex molecules. Resulting DNA-RNA duplex molecules from the reverse transcription reaction may be purified before use or may be used directly without purification. Examples of purification of the DNA-RNA duplex molecules after reverse transcription reaction include ethanol precipitation, column chromatography and gel filtration.

Figure 1:
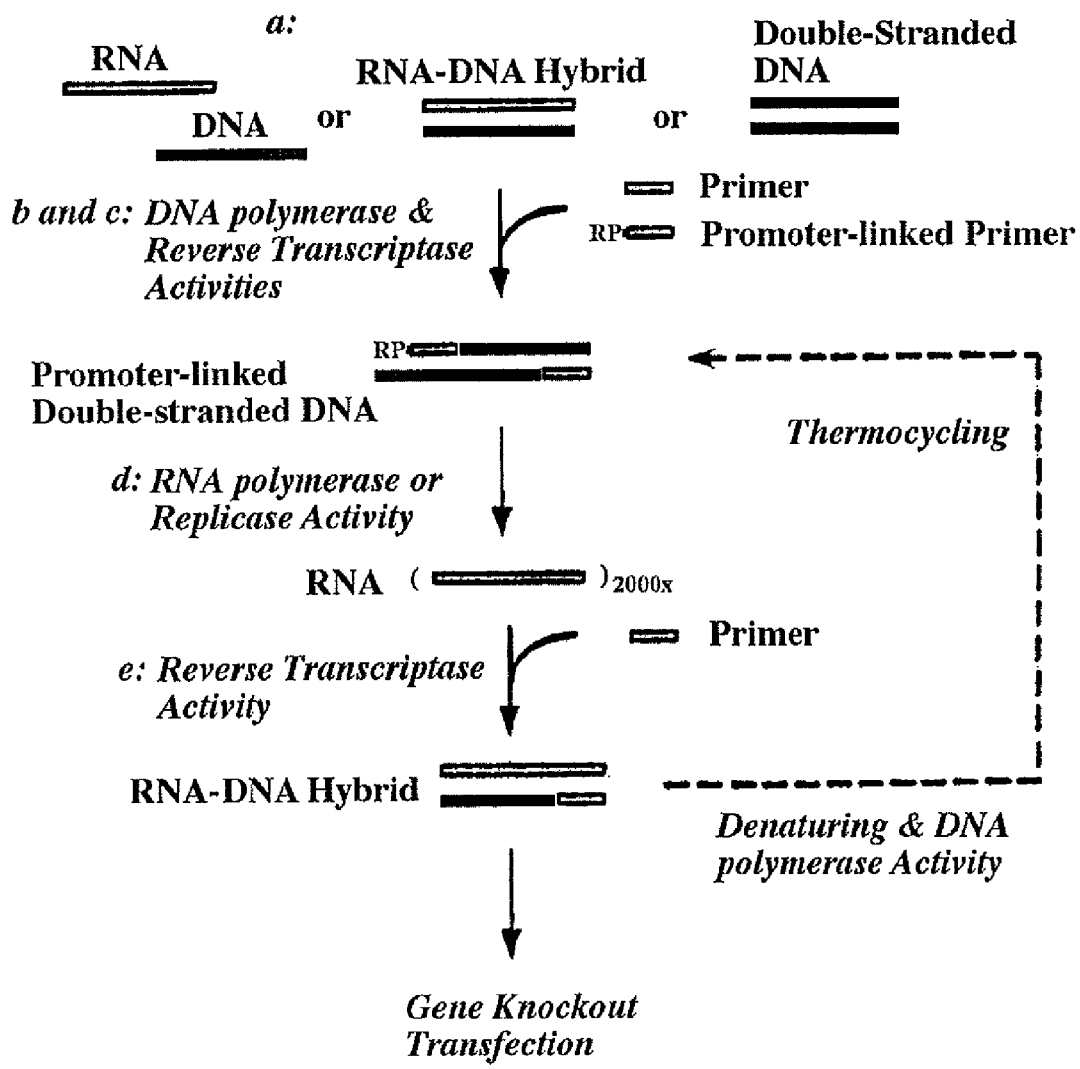
FIG. 1 shows a schematic representation of various enzymatic methods used for generating the DNA-RNA duplex agents.

Preferably, the DNA-RNA duplex may be generated by an improvement of the so-called RNA-PCR, described in U.S. Pat. No. 6,197,554 by common inventors in this application. As seen in FIG. 1, the starting material for generating the DNA-RNA duplex molecule can be any type of nucleic acid molecule such as single stranded DNA or RNA, double stranded DNA, or DNA-RNA duplexes. The modification of the RNA-PCR method disclosed in the '554 patent involves the use of a gene-specific primer and promoter-primer in the thermocycling procedure to amplify specific DNA-RNA sequences for gene knockout technologies. This thermocycling procedure preferably starts from reverse transcription of mRNAs with RNA promoter-containing primer(s) and Tth-like polymerases, followed by DNA double-stranding reaction with the same Tth-like polymerases. The resulting promoter-linked double-stranded DNAs may then serve as transcriptional templates for amplifying RNA amount up to 2000 fold/cycle by RNA polymerases. The thermocycling procedure can be repeated for more amplification of the DNA-RNA duplexes. (Again, as seen in FIG. 1, the starting material can be a double-stranded DNA, which would mean that instead of starting with a reverse transcriptase reaction, the double-stranded DNA is denatured, annealed with the promoter-linked primer, and extended using DNA polymerases such as Taq DNA polymerase to generate a double-stranded DNA having a RNA polymerase promoter sequence.)

The amplification cycling procedure of the present invention presents several advantages over prior amplification methods. First, DNA-RNA duplex probes from low-copy rare mRNA species can be prepared within three round of amplification cycling without mis-reading mistakes. Second, the DNA-RNA hybrid amplification is linear and does not result in preferential amplification of nonspecific gene sequences. Third, the RNA degradation is inhibited by thermostable enzymatic conditions with RNase inhibitors. Finally, the use of RNase H-free reverse transcriptase reduces the activity of RNase H and therefore preserves the integrity of the final DNA-RNA constructs. Unlike previous NASBA methods (Compton, *Nature* 350: 91-92 (1991)), this improved RNA-PCR procedure contains no RNase H activity, which usually destroys the RNA structure of a DNA-RNA duplex. Based on these advantages, high amount of pure and specific DNA-RNA duplexes can be prepared for transducing biological effects of interest in vitro, ex vivo as well as in vivo.

Figure 7:
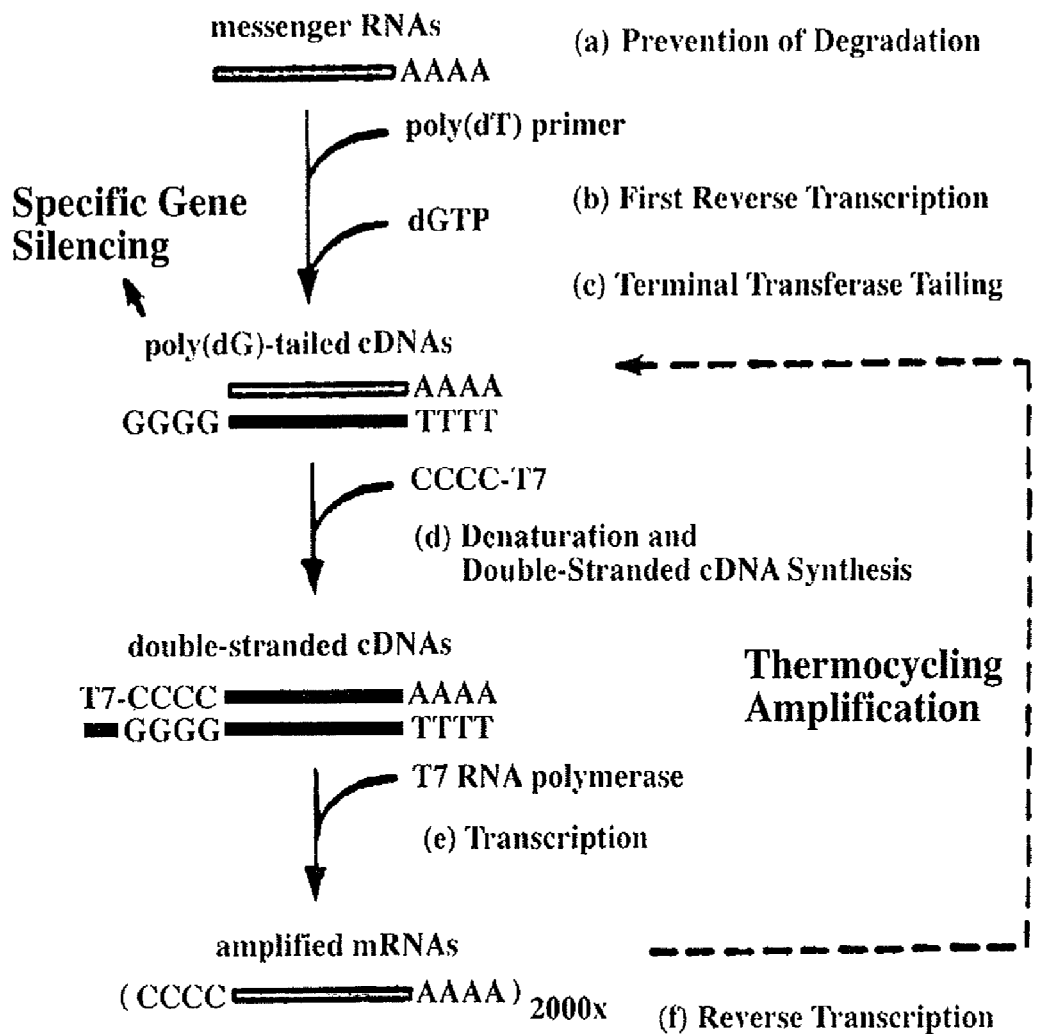
FIG. 7 shows a schematic representation for producing DNA-RNA duplexes using an enzymatic RNA-PCR reaction.

Another advantage of the preferred method, as exemplified in FIG. 7, is that labor and working time are largely reduced because of the high amplification efficiency of the bacteriophage RNA polymerases (up to 2000 folds/cycle) for in-vitro transcription. Also, such preparation of amplified DNA-RNA duplexes is less expensive and more efficient than traditional cDNA cloning with an expression-competent plasmid vector and then reverse transcription of the expressed RNA products. Most importantly, this RNA-PCR amplification procedure can be carried out in a micro-tube with only a few nucleic acid templates (0.2 pg). Taken together, these special features make the improved content of RNA-PCR as simple, fast, and inexpensive as a kit for concisely isolating amplified DNA-RNA duplex sequences for specific gene knockout as described in the present invention.

Although certain preferred embodiments of the present invention have been described, the spirit and scope of the invention is by no means restricted to what is described above. For example, within the general framework of a) one or more types of nucleic acid templates used; b) one or more specific primers for reverse transcription and polymerase extension reactions; c) one or more promoter-linked primers for transcription reactions; d) one or more enzymes for each step of reaction(s); e) one or more rounds of the cycling procedure for DNA-RNA hybrid amplification, there is a very large number of permutations and combinations possible, all of which are within the scope of the present invention.

In yet another example, the DNA-RNA duplex can be generated by a method comprising: a) providing: i) a solution comprising a nucleic acid template, ii) one or more primers sufficiently complementary to the sense conformation of the nucleic acid template, and iii) one or more promoter-linked primers sufficiently complementary to the antisense conformation of the nucleic acid template, and having an RNA promoter; b) treating the nucleic acid template with one or more primers under conditions such that a first DNA strand is synthesized; c) treating the first DNA strand with one or more promoter-linked primers under conditions such that a promoter-linked double-stranded nucleic acid is synthesized; d) treating the promoter-linked double-stranded nucleic acid under conditions such that essentially RNA fragments are synthesized; and e) treating RNA fragments with one or more primers under conditions such that DNA-RNA duplexes are synthesized. The steps of (b) through (e) may also be repeated for a sufficient number of cycles to obtain a desired amount of amplified duplex hybrid product.

The treating step in step (b) can also comprise heating the solution at a temperature above 90° C. to provide denatured nucleic acids. The treating step in step (c) can also comprise treating the first DNA strand with one or more promoter-linked primers at a temperature ranging from about 37° C. to about 70° C., depending on the annealing sequence region used. The treating step in step (c) can also comprise treating the DNA strand with one or more promoter-linked primers in the presence of a polymerase.

In one embodiment, the polymerase used in the above methods may include DNA-dependent DNA polymerases, RNA-dependent DNA polymerases, RNA polymerases, Taq-like DNA polymerase, Tth-like DNA polymerase, C. therm. polymerase, viral replicases, and combinations thereof. The viral replicases may include avian myeloblastosis reverse transcriptase, Moloney murine leukemia virus reverse transcriptase, and their derivatives that do not have RNase H activity, and Brome mosaic virus replicase, *Trichomonas vaginalis* virus replicase, Flock house virus replicase, Q beta replicase, and their mutants and/or combinations thereof.

The treating step in step (d) can also comprise treating the promoter-linked double-stranded nucleic acid with an enzyme having transcriptase activity at about 37° C. The enzyme having transcriptase activity can be selected from the group consisting of RNA polymerases and viral replicases. The RNA polymerases can be selected from the group consisting of T3 RNA polymerase, T7 RNA polymerase, SP6 RNA polymerase, and M13 RNA polymerase, Brome mosaic virus replicase, *Trichomonas vaginalis* virus replicase, Flock house virus replicase, Q beta replicase, and their mutants and/or combinations thereof.

As to the primers, the primers may be complementary to the 3'-ends of the antisense conformation of the nucleic acid template. In one embodiment, one or more primers comprise a sequence-specific primer homologous or complementary to the targeted gene transcript. The promoter-linked primers may include a sequence complementary to the 3'-ends of the sense conformation of the nucleic acid template and a sequence corresponding to the sequence of an RNA polymerase promoter. In one embodiment, one or more promoter-linked primers comprise a sequence-specific primer complementary to the targeted gene transcript, such as T7 promoter-linked poly(dT) primers. The promoter-linked double-stranded nucleic acid template can also include linear and circular promoter-containing double-stranded DNAs or promoter-linked single-stranded DNAs.

In one embodiment, the treating step in step (e) may comprise treating RNA fragments with one or more primers at a temperature ranging from about 35° C. to about 72° C., depending on the annealing sequence region used.

The synthesis of the DNA-RNA duplex molecule, in accordance with any of the above methods, may also include a step of incorporating one or more nucleotide analogs into the DNA or RNA portion of the DNA-RNA duplex to facilitate and increase the induction and onset of RNAi-related effects. The nucleotide analog is incorporated by either a chemical synthesizer or enzymatic reactions, or both. The nucleotide analog can be selected from the group consisting of ribonucleotide in the DNA construct, deoxynucleotide in the RNA construct, deoxyuracil (dU), inosine (I), xanthine(X), hypoxanthine (HX) and/or their derivative analogs in the hybrid duplex construct. Alternatively, the nucleotide analog can be generated by adding deaminase or acidic chemicals to the DNA-RNA duplex, resulting in derivatives selected from the group consisting of inosine (I) and its derivative analogs (See e.g., U.S. Pat. No. 6,130,040, which is hereby incorporated by reference).

Labeling of DNA-RNA duplexes may also be achieved by incorporation of labeled nucleotides or analogs during the reverse transcription of RNAs. The nucleotide sequences so generated are useful for tracking down the transfected cells in a large cell population. These labeled nucleotides are also capable of being probes in a variety of applications, such as Southern blots, dot hybridization, position cloning, nucleotide sequence detection, gene knockout transfection and so on. The incorporated nucleotide analogs also provide better protection of the DNA-RNA structures, resulting in more stability and effectiveness of the probe transfection. The nucleotide analog can be selected from the group consisting of biotin-labeled, digoxigenin-labeled, fluorescein-labeled, amino-methylcoumarin-labeled, tetramethyl-rhodamine-labed nucleotides and their derivatives.

DEFINITIONS

To facilitate understanding of the invention, a number of terms are defined below.

As used herein, the term "isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. If the "isolated" composition occurs as an intermediate composition in an in vitro process, "isolated" composition does not mean the intermediate composition but the desired end product intended to be introduced into a cell. For example, an intermediate DNA-RNA hybrid duplex that forms in an in-vitro transcription reaction is an intermediate and would not be "isolated." On the other hand, the end product of a reverse transcriptase reaction from an RNA creating a DNA-RNA duplex construct would be "isolated" even without purification of the hybrid from the enzymes, templates, nucleotides, primers, and buffers present in the reaction.

As used herein, the terms "complementary" or "complementarity" or "complementation" are used in reference to polynucleotides (i.e., a sequence of nucleotides) related by the base-pairing rules. For example, the sequence "A-G-T" is complementary to the sequence "T-C-A," and also to "T-C-U." Complementation can be between two DNA strands, a DNA and an RNA strand, or an RNA and another RNA strand. Complementarity may be "partial" or "complete" or "total". Partial complementarity or complementation occurs when only some of the nucleic acid bases are matched according to the base pairing rules. Complete or total complementarity or complementation occurs when the bases are completely matched between the nucleic acid strands. The degree of complementarity between nucleic acid strands has significant effects on the efficiency and strength of hybridization between nucleic acid strands. This is of particular importance in amplification reactions, as well as in detection methods which depend upon binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

As used herein, the term "homologous" or "homology" refers to a polynucleotide sequence having similarities with a mRNA sequence or naturally occurring RNA sequence such as t-RNA; rRNA or RNA genome of an RNA virus. A nucleic acid sequence may be partially or completely homologous to a particular mRNA sequence, for example. Homology may also be expressed in percentage as determined by the number of similar nucleotides over the total number of nucleotides.

As used herein, the term "sDNA" refers to a single stranded DNA that is homologous to a mRNA sequence, while the term "sRNA" refers to a single stranded RNA that is the same as or homologous to a mRNA sequence. The term "aDNA" and "cDNA" refers to a single stranded DNA that is complementary to a mRNA sequence, while the term "aRNA" refers to a single stranded RNA that is complementary to a mRNA sequence.

As used herein, the term "sense conformation" refers to a nucleic acid sequence in the same sequence order and composition as its homolog mRNA. The sense conformation is indicated as a "+" symbol, or with a "s" in front of the DNA or RNA, e.g., "sDNA" or "sRNA".

As used herein, the term "antisense" refers to a nucleic acid sequence complementary to its respective mRNA molecule or a naturally occurring RNA molecule such as t-RNA, rRNA, or viral RNA. The viral RNA may be the genome of an RNA virus and may or may not encode for a functional protein. For example, the antisense RNA (aRNA) may refer to a ribonucleotide sequence complementary to a mRNA sequence, encoding for a protein, in an A-U and C-G composition, and also in the reverse orientation of the mRNA. The antisense conformation is indicated as a "−" symbol or with a "a" in front of the DNA or RNA, e.g., "aDNA" or "aRNA."

As used herein, the term "template" refers to a nucleic acid molecule being copied by a nucleic acid polymerase or a chemical synthesizer. A template can be single-stranded, double-stranded or partially double-stranded, depending on the polymerase or chemical reaction. The synthesized copy is complementary to the template, or to at least one strand of a double-stranded or partially double-stranded template. Both RNA and DNA are usually synthesized in the 5' to 3' direction (3',5'-linkages); however, some chemical synthesizers do provide the 5' to 2' phosphodiester linkages (2',5'-linkages). The 2',5'-linked and 3',5'-linked RNA/DNA share the same functional properties to the purpose of the present invention. The two strands of a nucleic acid duplex are always aligned so that the 5' ends of the two strands are at opposite ends of the duplex (and, by necessity, so then are the 3' and/or 2' ends).

As used herein, the term "nucleic acid template" refers to a double-stranded DNA molecule, double-stranded RNA molecule, hybridized molecule such as DNA-RNA or RNA-DNA duplex, or single-stranded DNA or RNA molecule.

As used herein, the term "palindromic sequence" refers to a segment of single- or double-stranded nucleic acid sequence in which the base sequence(s) of the strand duplex exhibit about twofold rotational symmetry about an axis. For example, the duplex of "TTAGCAC GTGCTAA" and "AATCGTG CACGATT".

As used herein, the term "primer" refers to an oligonucleotide complementary to a template. The primer complexes with the template to give a primer/template complex for initiation of synthesis by a DNA polymerase. The primer/template complex is extended by the addition of covalently bonded bases linked at its 3' end, which are complementary to the template in DNA synthesis. The result is a primer extension product. Virtually all known DNA polymerases (including reverse transcriptases) require complementary binding of an oligonucleotide to a single-stranded template ("priming") to initiate DNA synthesis.

As used herein, the term "promoter-linked primer" refers to an RNA-polymerase-promoter sense sequence coupled with a gene-specific complementary sequence in its 3'-end for annealing to the antisense conformation of a nucleic acid template.

As used herein, the term "DNA-dependent DNA polymerase" refers to an enzyme that synthesizes a complementary DNA copy from a DNA template. Examples are DNA polymerase I from *E. coli* and bacteriophage T7 DNA polymerase. Under suitable conditions a DNA-dependent DNA polymerase may synthesize a complementary DNA copy from an RNA template.

As used herein, the terms "DNA-dependent RNA polymerase" and "transcriptase" refer to enzymes that synthesize multiple RNA copies from a double-stranded or partially-double stranded DNA molecule having a promoter sequence. Examples of transcriptases include, but are not limited to, DNA-dependent RNA polymerase from *E. coli* and bacteriophages T7, T3, and SP6.

As used herein, the terms "RNA-dependent DNA polymerase" and "reverse transcriptase" refer to enzymes that synthesize a complementary DNA copy from an RNA template. All known reverse transcriptases also have the ability to make a complementary DNA copy from a DNA template. Thus, reverse transcriptases are both RNA-dependent and DNA-dependent DNA polymerases. As used herein, the term "RNase H" refers to an enzyme that degrades the RNA portion of an RNA/DNA duplex. RNase H may be endonucleases or exonucleases. Most reverse transcriptase enzymes normally contain an RNase H activity in addition to their polymerase activity. However, other sources of the RNase H are available without an associated polymerase activity. The degradation may result in separation of RNA from a RNA/DNA complex. Alternatively, the RNase H may simply cut the RNA at various locations such that portions of the RNA melt off or permit enzymes to unwind portions of the RNA.

As used herein, the terms "hybridize" and "hybridization" refer to the formation of complexes between nucleotide sequences which are sufficiently complementary to form complexes via Watson-Crick base pairing. Where a primer (or splice template) "hybridizes" with target (template), such complexes (or hybrids) are sufficiently stable to serve the priming function required by the DNA polymerase to initiate DNA synthesis.

As used herein, the term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term "gene" encompasses both cDNA and genomic forms of a gene. A genomic form or clone of a gene contains the coding region interrupted with non-coding sequences termed "intervening regions" or "intervening sequences."

As used herein, the term "gene silencing" refers to a phenomenon whereby a function of a gene is completely or partially inhibited. Throughout the specification, the terms "silencing," "inhibition," "quelling," "knockout" and "suppression," when used with reference to gene expression or function, are used interchangeably.

As used herein, the term "oligonucleotide" is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, the term "transfection" refers to the introduction of foreign DNA into eukaryotic cells. Transfection can be accomplished by a variety of means known to the art, including, but not limited to, calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

A primer is selected to be "substantially" or "sufficiently" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the term "amplification" refers to nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that will process only specific sequences of nucleic acid in a heterogeneous mixture of nucleic acid. For example, in the case of Qb replicase, MDV-1 RNA is the specific template for the replicase (Kacian et al. (1972) *Proc. Natl. Acad. Sci. USA* 69, 3038). Other types of nucleic acids will not be amplified by this enzyme. Similarly, in the case of T7 RNA polymerase, this amplification enzyme has a stringent specificity for its own promoters (Chamberlin et al. (1970) *Nature* 228, 227). Taq and Pfu polymerases, by virtue of their ability to function at high temperature display high specificity for the sequences bounded, and thus defined by the primers.

As used herein, the terms "amplifiable nucleic acid" and "amplified products" refer to nucleic acids which may be amplified by any enzymatic or chemical method.

As used herein, the term "probe" refers to an oligonucleotide (i.e., a sequence of nucleotides) which is capable of hybridizing to another oligonucleotide of interest, whether occurring naturally as in a purified restriction digest or produced synthetically, recombinantly or by enzymatic amplification. A probe may be single-stranded or double-stranded. Probes are useful in the detection, identification and isolation of particular gene sequences.

As used herein, the term "enzymatic amplification" (such as RT, PCR, NASBA and RNA-PCR) refers to a method for increasing the concentration of a segment in a target sequence from a mixture of genomic DNAs without cloning or purification (U.S. Pat. Nos. 4,683,195; 4,683,202; 4,965,188 (PCR); U.S. Pat. No. 5,888,779 (NASBA); U.S. Pat. No. 6,197,554 (RNA-PCR) and WO 00/75356, hereby incorporated by reference). This process for amplifying the target sequence consists of introducing a large excess of two oligonucleotide primers to the DNA mixture containing the desired target sequence, followed by a precise sequence of thermal cycling in the presence of DNA and/or RNA polymerase(s). The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. Because the desired amplified segments of the target sequence become the predominant sequences (in terms of concentration) in the mixture, they are said to be amplified.

With enzymatic amplification, it is possible to amplify a single copy of a specific target sequence in genomic DNA to a level detectable by several different methodologies (e.g., incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR and RNA-PCR process itself are, themselves, efficient templates for subsequent PCR and RNA-PCR amplifications.

As used herein, the term "portion" when in reference to a protein or nucleic acid sequence refers to fragments of that protein or nucleic acid sequence. Fragments of a protein can range in size from four amino acid residues to the entire amino acid sequence minus one amino acid.

The term "nucleotide analog" as used herein refers to modified or non-naturally occurring nucleotides such as deoxyuracil, inosine, xanthine, hypoxanthine, labeled nucleotides, 7-deaza-dNTP, methylthio-linked nucleotide, phosphothio-linked nucleotide, hexose-containing nucleotide, morpholino nucleotide, peptide nucleic acid (PNA), etc. Nucleotide analogs include base analogs and comprise modified backbone forms of deoxyribonucleotides as well as ribonucleotides, such as ribonucleotide(s) in a DNA sequence and deoxyribonucleotide(s) in an RNA sequence.

The term "Northern blot," as used herein refers to the analysis of RNA by electrophoresis of RNA on agarose gels to fractionate the RNA according to size, followed by transfer of the RNA from the gel to a solid support such as nitrocellulose or a nylon membrane. The immobilized RNA is then probed with a labeled probe to detect RNA species complementary to the probe used. Northern blots are a standard tool of molecular biologists (Sambrook et al., (1989) *Molecular Cloning*, $2^{nd}$ Ed., Cold Spring Harbor Laboratory Press, pp 7.39-7.52).

As used herein, the term "Southern blot" refers to the analysis of DNA on agarose or acrylamide gels to fractionate the DNA according to size, followed by transfer of the DNA from the gel to a solid support such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., supra).

The term "virus" refers to obligate, ultramicroscopic, intracellular parasites incapable of autonomous replication (i.e., replication requires the use of the host cell's machinery).

As used herein, the terms "Taq-like polymerase" and "Taq polymerase" refer to Taq DNA polymerase and derivatives. Taq DNA is widely used in molecular biology techniques including recombinant DNA methods. For example, various forms of Taq have been used in a combination method which utilizes PCR and reverse transcription (See e.g., U.S. Pat. No. 5,322,770, incorporated herein in its entirety by reference). DNA sequencing methods, which utilize Taq DNA polymerase have also been described. (See e.g., U.S. Pat. No. 5,075,216, incorporated herein in its entirety by reference).

As used herein, the terms "Tth-like polymerase" and "Tth polymerase" refer to polymerase isolated from *Thermus thermophilus*. Tth polymerase is a thermostable polymerase that can function as both reverse transcriptase and DNA polymerase (Myers and Gelfand, (1991) *Biochemistry* 30, 7662-7666). It is not intended that the methods of the present invention be limited to the use of Taq-like or Tth-like polymerases. Other thermostable DNA polymerases which have a 5' to 3' exonuclease activity (e.g., Tma, Tsps17, TZ05, Tth and Taf) can also be used to practice the compositions and methods of the present invention.

As used herein, "reverse transcription" means the synthesis of a DNA molecule from an RNA molecule using an enzymatic reaction in vitro. For example, the RNA molecule may be primed with a primer that is complementary to the RNA molecule and the DNA molecule is synthesized by extending using a reverse transcriptase such as Tth DNA polymerase with reverse transcription activity, MMLV reverse transcriptase, AMV reverse transcription, and any other enzymes that have the ability to synthesize DNA molecule from an RNA molecule as template.

As used herein, "in vitro transcription" means the synthesis of an RNA molecule from a nucleic acid template molecule using an enzymatic reaction in vitro. For example, the nucleic acid template may be a double-stranded DNA sequence and comprises an RNA polymerase promoter such as T7, SP6, T3, or any other enzyme promoter for synthesis of RNA from the template.

EXAMPLES

The following examples serve to illustrate certain preferred embodiments and aspects of the present invention and are not to be construed as limiting the scope thereof.

In the experimental disclosure which follows, the following abbreviations apply: M (molar); mM (millimolar); μm (micromolar); mol (moles); pmol (picomolar); gm (grams); mg (milligrams); L (liters); ml (milliliters); μl (microliters); ° C. (degrees Centigrade); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); and ATCC (American Type Culture Collection, Rockville, Md.).

All routine techniques and DNA manipulations, such as gel electrophoresis, were performed according to standard procedures. (See Sambrook et at., supra). All enzymes and buffer treatments were applied following the manufacture's recommendations (Roche Biochemicals, Indianapolis, Ind.). For Northern blots, mRNAs were fractionated on 1% formaldehyde-agarose gels and transferred onto nylon membranes (Schleicher & Schuell, Keene, N.H.). Probes were labeled with the Prime-It II kit (Stratagene, La Jolla, Calif.) by random primer extension in the presence of [$^{32}$P]-dATP (>3000 Ci/mM, Amersham International, Arlington Heights, and purified with Micro Bio-Spin chromatography columns (BIO-RAD, Hercules, Calif.). Hybridization was carried out in the mixture of 50% freshly deionized formamide (pH 7.0), 5×Denhardt's solution, 0.5% SDS, 4×SSPE and 250 mg/ml denatured salmon sperm DNAs (18 hr, 42° C.). Membranes were sequentially washed twice in 2×SSC, 0.1% SDS (15 min, 25° C.), and once each in 0.2×SSC, 0.1% SDS (15 min, 25° C.); and 0.2×SSC, 0.1% SDS (30 min, 65° C.) before autoradiography by films.

For cell fixation and permeabilization, MCF-7 cells, a breast cancer cell line, were grown in MEM medium supplemented with 10% fetal calf serum. A sample containing cells cultured in a 60 mm dish (70% full of cells) was trypsinized, collected and washed three times in 5 ml phosphate buffered saline (PBS, pH 7.2) at room temperature. After washing, the cells were suspended in 1 ml of ice-cold 10% formaldehyde solution in 0.15M NaCl. After one-hour incubation on ice with occasional agitation, the cells were centrifuged at 13,000 rpm for 2 min, and washed three times in ice-cold PBS with vigorous pipetting. The collected cells were resuspended in 0.5% non-ionic detergents, such as (octylphenoxy)-polyethanol or polyoyethylenesorbitan (Sigma), and incubated for one hour with frequent agitation. The cells were washed three times in ice-cold PBS containing 0.1M glycine, then resuspended in 1 ml of the same buffer with vigorous pipetting in order to be evenly separated into small aliquots and stored at −70° C. for up to a month.

Example 1

Cell Fixation And Permeabilization

LNCaP cells, a prostate cancer cell line, were grown in RPMI 1640 medium supplemented with 2% fetal calf serum. A sample containing cells cultured in a 60 mm dish (70% full of cells) was trypsinized, collected and washed three times in 5 ml phosphate buffered saline (PBS, pH 7.2) at room temperature. After washing, the cells were suspended in 1 ml of ice-cold 10% formaldehyde solution in 0.15M NaCl. After one-hour incubation on ice with occasional agitation, the cells were centrifuged at 13,000 rpm for 2 min, and washed three times in ice-cold PBS with vigorous pipetting. The collected cells were resuspended in 0.5% non-ionic detergents, such as (octylphenoxy)-polyethanol or polyoyethylenesorbitan (Sigma), and incubated for one hour with frequent agitation. The cells were washed three times in ice-cold PBS containing 0.1M glycine, then resuspended in 1 ml of the same buffer with vigorous pipetting in order to be evenly separated into small aliquots and stored at −70° C. for up to a month.

Example 2

In-Cell Reverse Transcription And Poly-(N) Tailing of cDNAs

For reverse transcription of mRNAs in cells, twenty of the fixed cells were thawed, resuspended in 20 µl of ddH$_2$O, heated to 65° C. for 3 min and then cooled on ice. A 50 µl RT reaction was prepared, comprising 5 µl of 10× in-cell RT buffer (1.2M KCl, 0.5M Tris-HCl, 80 mM MgCl$_2$, 10 mM dithiothreitol, pH 8.1 at 42° C.), 5 µl of 5 mM dNTPs, 25 pmol oligo(dT)n-T7 promoter (SEQ ID NO. 1), 80 U RNase inhibitor and above cold cells. After reverse transcriptase (40 U) was added, the RT reaction was mixed and incubated at 55° C. for three hours. The cells were then washed once with PBS and resuspended in a 50 µl tailing reaction, comprising 2 mM dGTP, 10 µl of 5× tailing buffer (250 mM KCl, 50 mM Tris-HCl, 7.5 mM MgCl$_2$, pH 8.3 at 20° C.). The tailing reaction was heated at 94° C. for 3 min and then chilled in ice for mixing with terminal transferase (20 U), following further incubation at 37° C. for 20 min. Final reaction was stopped at 94° C. for 3 min. The reaction mixture was chilled in ice immediately, which formed the poly(N)-tailed cDNAs.

Example 3

Single-Cell mRNA Amplification

To increase the intracellular copies of whole mRNAs, the T7 promoter region of a poly(N)-tailed cDNA was served as a coding strand for the amplification by T7 RNA polymerase (Eberwine et al., *Proc. Natl. Acad. Sci. USA* 89: 3010-3014 (1992)). As few as one cell in 5 µl of the above tailing reaction can be used to accomplish full-length aRNA amplification. An in-cell transcription reaction was prepared on ice, containing 25 pmol poly(dC)-12 mer primer (SEQ ID NO. 2), 1 mM dNTPs, Pwo DNA polymerase (5 U), 5 µl of 10× Transcription buffer (Roche), 2 mM rNTPs and T7 RNA polymerase (2000 U). The hybridization of 20 mer primer to the poly(N)-tailed cDNAs was incubated at 65° C. for 5 min to complete second strand cDNA synthesis and then RNA polymerase was added to start transcription. After four-hour incubation at 37° C., the cDNA transcripts were isolated from both cells and supernatant, to be directly used in the following reverse transcription. The reaction was finally stopped at 94° C. for 3 min and chilled in ice.

Example 4

In Vitro Reverse Transcription And PCR Amplification

A 50 µl RT reaction was prepared, comprising 5 µl of 10×RT buffer (300 mM KCl, 0.5M Tris-HCl, 80 mM MgCl$_2$, 10 mM dithiothreitol, pH 8.3 at 20° C.), 5 µl of 5 mM dNTPs, 25 pmol oligo(dC)$_{10}$-T7 promoter mix (SEQ ID NO. 3, 4 and 5), 80 U RNase inhibitor, ddH2O and 5 µl of the above aRNA containing supernatant. After reverse transcriptase (40 U) was added, the RT reaction was vortexed and incubated at 55° C. for three hours. The resulting products of RT can be directly used in following PCR reaction (50 □D, comprising 5 µl of 10×PCR buffer (Roche), 5 µl of 2 mM dNTPs, 25 pmol T7-20 mer primer, 25 pmol poly(dT)-26 mer primer (SEQ ID NO. 6), ddH2O, 5 µl of above RT product and 3 U of Taq/Pwo long-extension DNA polymerase. The PCR reaction was subjected to thirty cycles of denaturation at 95° C. for 1 min, annealing at 55° C. for 1 min and extension at 72° C. for 3 min. The quality of final amplified cDNA library (20 µl) was assessed on a 1% formaldehyde-agarose gel, ranging from 100 bp to above 12 kb.

Example 5

RNA-PCR

Pre-cycling procedures. Primers used in RNA-PCR were as follows: a poly(dT)-26 primer (5'-TTTTTTTTTT TTTTTTTTTT TTTTTT-3') (SEQ ID NO. 6) and an oligo (dC)$_{10}$N-promoter primer mixture comprising equal amounts of oligo(dC)$_{10}$G-T7 primer (5'-dCCAGTGAATT GTAATACGAC TCACTATAGG GAAC$_{10}$G-3') (SEQ ID NO. 3); oligo(dC)$_{10}$A-T7 primer (5'-dCCAGTGAATT GTAATACGAC TCACTATAGG GAAC$_{10}$A-3') (SEQ ID NO. 4); and oligo(dC)$_{10}$T-T7 primer (5'-dCCAGTGAATT GTAATACGAC TCACTATAGG GAAC$_{10}$T-3') (SEQ ID NO. 5). The poly(dT)-26 primer was used to reverse transcribe mRNAs into first-strand cDNAs, while the oligo(dC) 10N-promoter primers functioned as a forward primer for second-strand cDNA extension from the poly(dG) end of the first-strand cDNAs and therefore RNA promoter incorporation. All oligonucleotides were synthetic and purified by high performance liquid chromatography (HPLC).

For in situ hybridization and cell preparations, fresh formaldehyde prefixed paraffin-embedded sections were dewaxed, dehydrated and refixed with 4% PFA, and then permeabilized with proteinase K (10 µg/ml; Roche) after rinsing with 1×PBS. In situ hybridization was achieved with a denatured hybridization mixture within a 200 µl coverslip chamber, containing 40% formamide, 5×SSC, 1×Denhardt's reagent, 50 µg/ml salmon testis DNA, 100 µg/ml tRNA, 120 pmol/ml poly(dT)-26 primer, 10 pmol/ml biotin-labeled activin antisense probe (~700 bases in size) and tissue. After 10 h incubation at 65° C., sections were washed once with 5×SSC at 25° C. for 1 h and once with 0.5×SSC, 20% formamide at 60° C. for 30 min to remove unbound probes. A pre-heating step (68°, 3 min) immersing the sections in a mild denaturing solution (25 mM Tris-HCl, pH 7.0, 1 mM EDTA, 20% formamide, 5% DMSO and 2 mM ascorbic acid) was performed to minimize secondary structures (including crosslinks) and to reduce the background. After the temperature was lowered to 45° C., 2,5-diaziridinyl-1,4-benzoquinone (200 μM; Sigma Chemical Co., St. Louis, Mo.) was added to each incubation for a further 30 min. Finally, 0.1× SSC, 20% formamide was applied at 60° C. for 30 min to clean sections for chromogenic detection with straptavidin-alkaline phosphatase and Fast Red staining (Roche Biochemicals, Indianapolis, Ind.). Positive and negative results were observed and recorded under a microscope. RNase-free enzymes and DEPC-treated materials were required throughout the procedure.

RNA-PCR. For amplification of intracellular mRNAs, more than 20 fixed cells were preheated at 94° C. for 5 min and applied to a reverse transcription (RT) reaction mixture (50 μl) on ice, comprising 10 μl of 5×RT&T buffer [100 mM Tris-HCl, pH 8.5 at 25° C., 600 mM KCl, 300 mM $(NH_4)_2SO_4$, 25 mM $MgCl_2$, 5 M betaine, 35 mM dithiothreitol, 10 mM spermidine and 25% dimethylsulphoxide (DMSO)], 1 μM poly(dT)-26 primer, dNTPs (1 mM each dATP, dGTP, dCTP and dTTP) and RNase inhibitors (10 U). After 6 U *Caxboxydothernius hydrogenoformans* (*C. therm.*) polymerase (Roche) was added, the reaction was incubated at 52° C. for 3 min and shifted to 65° C. for another 30 min. The first-strand cDNAs so obtained were collected with a Microcon-50 microconcentrater filter, washed once with 1×PBS and suspended in a tailing reaction (50 μl), comprising 10 μl of 5× tailing buffer (250 mM KCl, 100 mM Tris-HCl, 4 mM $CoCl_2$, 10 mM $MgCl_2$, pH 8.3 at 20° C.) and 0.5 mM dGTP. After 75 U terminal transferase (Roche) was added, the reaction was incubated at 37° C. for 15 min, stopped by denaturation at 94° C. for 2 min and instantly mixed with 1 μM oligo(dC)$_{10}$-T7 primer mixture. After briefly centrifuging, 3.5 U Taq DNA polymerase (Roche) and 1 mM of each of the dNTPs was added to form promoter-linked double-stranded cDNAs at 52° C. for 3 min, and then 72° C. for 7 min. The cells were broken by adding 1 vol of 2% (octylphenoxy)-polyethanol polyoyethylenesorbitan for 10 min, and then the double-stranded cDNAs were washed and recollected with a microcon-50 in autoclaved ddH2O. This completed the precycling steps for the following cycling amplification.

A transcription reaction (50 μl) was prepared, containing 10 μl of 5×RT&T buffer, rNTPs (1 mM each ATP, GTP, CTP and UTP), RNA inhibitors (10 U), T7 RNA polymerase (200 U; Roche) and the double-stranded cDNAs. After 2-hour incubation at 37°, the cDNA transcripts were isolated with a microcon-50 filter in 20 μl of DEPC-treated TE buffer (pH 7.0) and used directly for the next round of RNA-PCR without the tailing reaction, containing 10 μl of 5×RT&T buffer, 1 μM poly(dT)-26 primer, 1 μM oligo(dC)$_{10}$-T7 primers, dNTPs (1 μM each), rNTPs (1 μM each), *C. therm.* polymerase, Taq DNA polymerase and the transcription products (20 pg). T7 RNA polymerase was renewed in every transcription step due to prior denaturation. The quality of mRNA products (20 μg) after three rounds of amplification was assessed on a 1% formaldehyde-agarose gel.

Example 6

Thermostable Cycling Amplification Procedure

Following a RNA-PCR procedure similar to the Examples 1-4 and 5, few fixed and permeabilized cells from chicken embryonic fibroblasts (CEF) were applied to a reaction mixture (20 ml) on ice, comprising 2 μl of 10×RT&T buffer (400 mM Tris-HCl, pH 8.3 at 25° C., 400 mM NaCl, 80 mM $MgCl_2$, 5M betaine, 100 mM DTT and 20 mM spermidine), 1 μM Shh-antisense primer (SEQ ID. NO. 7), 1 μM Shh-sense promoter-primer (SEQ ID. NO. 8), 2 μM rNTPs, 2 μM dNTPs and RNase inhibitors (10 U). After *C. therm.*/Taq DNA polymerase mixture (4 U) was added, the reaction was incubated at 52° C. for 3 min, at 65° C. for 30 min, at 94° C. for 3 min, at 52° C. for 3 min, and then at 68° C. for 3 min. A transcription reaction was prepared by adding T7 RNA polymerase (200 U) and a therm. polymerase (6 U) mixture into the above reaction. After one-hour incubation at 37° C., the resulting RNA transcripts were continuously reverse-transcribed into RNA-DNA duplexes at 52° C. for 3 min, and then at 65° C. for 30 min, so as to provide RNA-DNA duplexes. The quality of amplified RNA-DNA duplex products can be assessed on a 1% formaldehyde-agarose gel (Lin et at., Nucleic Acid Res. (1999)). The Shh DNA-RNA probes so obtained were designed to target a highly conserved region of the avian Sonic Hedge Hog (Shh) gene (NCBI accession number NM204821).

Example 7

Liposomal Transfection Procedure

Figure 8:
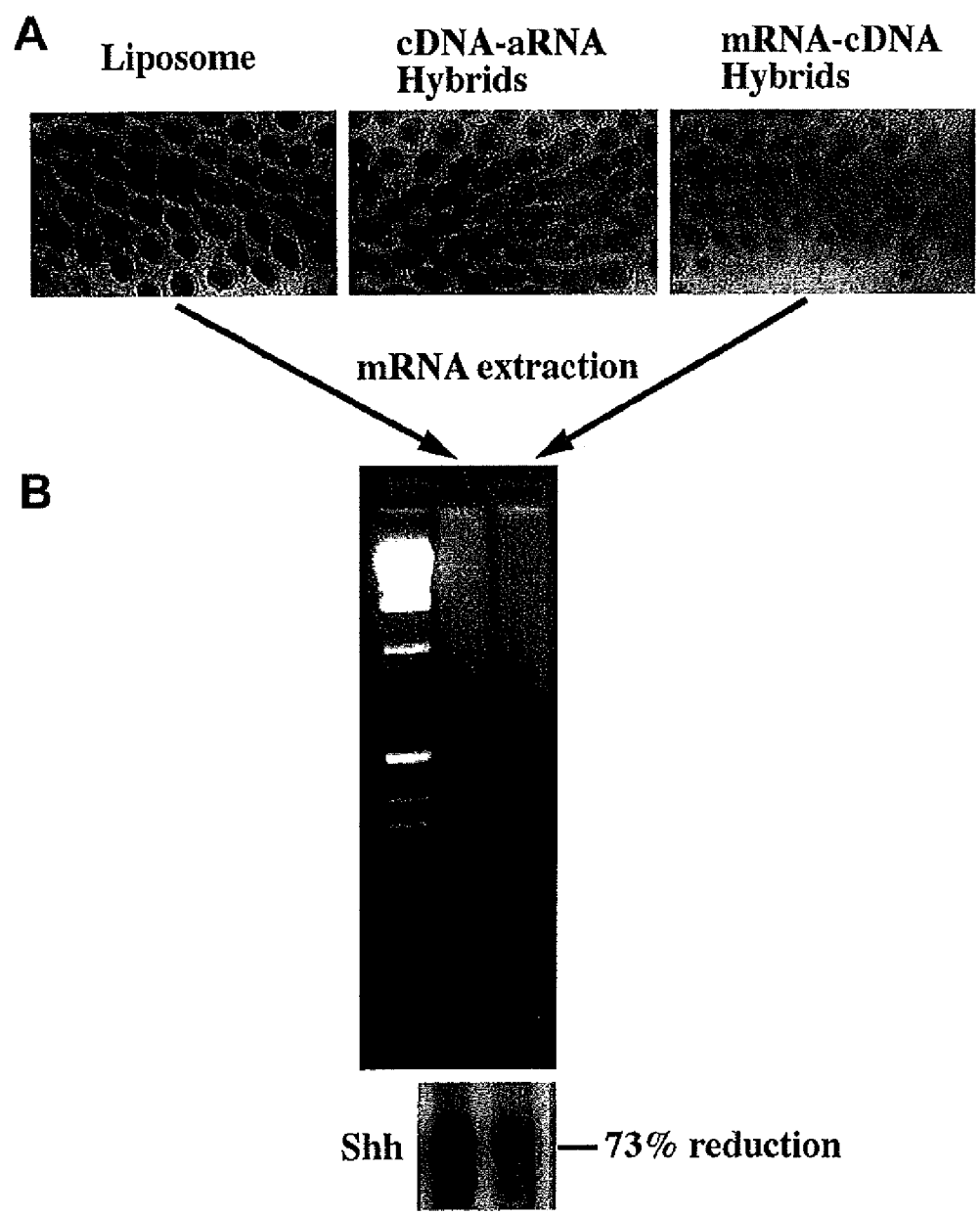
FIG. 8 shows Northern results of blank control and RNA-DNA duplexes in one embodiment of the present invention.

An RNA-DNA Shh probe (10 μg) was dissolved in 75 μl of Hepes buffer (pH 7.4). The resulting solution was mixed with 50 μl of DOTAP® liposome (1 μg/ml, Roche Biochemicals) on ice for 30 min., then subsequently applied to 60 mm diameter culture dishes containing four or five chicken skin explants. The skin explants were grown in HBSS medium. After a 36-hour incubation, the disturbance of feather growth is observed only in the mRNA-cDNA set while the blank-liposomal control has no effects (FIG. 8A). The Northern blot results of blank control and treated (as shown in mRNA-cDNA) set showed that a 73% gene silencing effect occurred 36 hour after the RNA-DNA Shh probe transfection (FIG. 8B). This result also demonstrates that the effectiveness of DNA-RNA duplex-mediated gene silencing is sequence-dependent and strand-specific (Bateman J R and Wu C T. (2007) *Bioessays* 29, 382-385).

Example 8

Gene Silencing Using A Chicken Embryo Model

This Example shows the effectiveness of a RNA-DNA strategy to knockout gene expression in vivo, using a developing chicken embryo as a model. In this example, β-catenin expression was targeted in the skin and liver of developing chick embryos. The RNA-DNA duplexes used for knocking □-catenin expression in vivo can be generated using the improved RNA-PCR technology discussed above.

For knocking out β-catenin gene expression, a double-stranded DNA template fragment, a pair of primers was designed based on the β-catenin cDNA sequence. Amplification of the RNA-DNA probes for targeting β-catenin (NCBI accession number NM205081 aa 306-644) required four primers (i.e., primers A-D). The upstream (A) primer comprises the sequence 5'-ATGGCAATCAAGAAAGTAAGC-3' (SEQ ID. NO. 9). The downstream (B) primer comprises the sequence 5'-GTACAACAACTGCACAAATAG-3' (SEQ ID. NO. 10). Another set of primers was required for the generation of the desired duplexes. The (C) primer was generated by adding the T7 promoter (RP) before the 5' end of the (A) primer. The (D) primer was generated by adding the T7 promoter before the 5' end of the (B) primer.

For sRNA-aDNA templates, B and C primers were used as primers in a polymerase chain reaction to generate promoter-linked double stranded cDNA. The promoter-linked double stranded cDNA was transcribed with T7 RNA polymerase for 2 h, and AMV reverse transcriptase for 1 hour Subsequently, the D-RNAi agents were collected by filtration over a Microcon 50 (Amicon, Bedford, Mass.) column and eluted with 20 µl of elution buffer (20 mM HEPES). The final concentration of D-RNAi is approximately 25 nM.

For the sDNA-aRNA template, A and D primers were used in a similar procedure as described above in the opposite orientation. The size of the RNA-DNA duplexes was then determined on a 1% agarose gel. The hybrids were kept at −20° C. until use.

Fertilized eggs were obtained from SPAFAS farm (Preston, Conn.) and incubated in humidified incubator (Humidaire, New Madison, Ohio). At designated dates, eggs were put under a dissection microscope and the egg shells were sterilized. The shells were carefully cracked open and a window was made to get access to the embryos.

Figure 9:
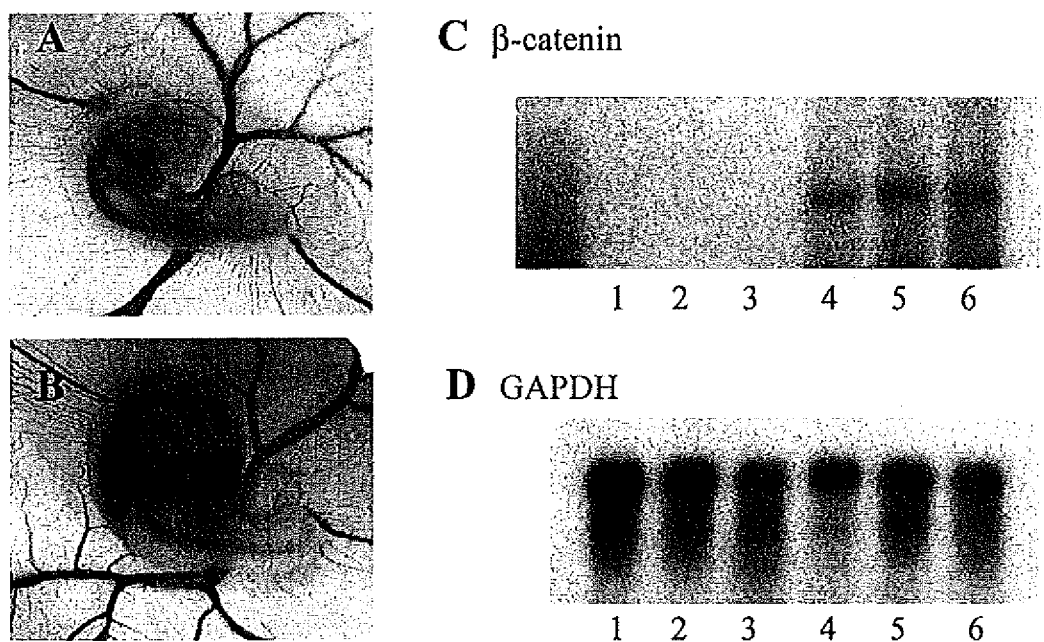
FIG. 9 shows the silencing effect of in vivo delivery of RNA-DNA duplexes on targeted gene expression, in one embodiment of the present invention.

Using embryonic day three chicken embryos, either sRNA-aDNA or sDNA-aRNA (25 nM) was injected into the ventral body cavity, close to where the liver primordia would form. The sRNA-aDNA probe was mixed with DOTAP liposome (Roche, Indianapolis, Ind.) at a ratio of 3:2. A 10% (v/v) fast green solution was added before the injection to increase visibility (FIG. 9B). The mixtures were injected into the ventral side near the liver primordia and below the heart using heat pulled capillary needles. After injection, the eggs were sealed with scotch tape and put back into a humidified incubator (Lyon Electric Company, Chula Vista, Calif.) at 39-40° C. until the harvesting time.

At designated days after injection, the embryos were removed, examined and photographed under a dissection microscope. While there are malformations, the embryos survived and there was no overt toxicity or overall perturbation of embryo development. The liver was closest to the injection site and is most dramatically affected in its phenotypes. Other regions, particularly the skin, are also affected by the diffused nucleotides.

Selected organs were removed and total RNAs were collected with an RNeasy kit (Qiagen, Valencia, Calif.) for Northern analysis. RNAs were fractionated in an RNase free polyacrylamide gel (1%) and then transferred to Nylon membranes for 16-18 h. The tested gene was hybridized with a radiolabeled probe, and an autoradiograph was exposed. Northern blot hybridizations using RNA from dissected livers showed that β-catenin in the control livers remained expressed (lane 4-6, FIG. 9C), whereas the level of β-catenin mRNA was decreased dramatically (lane 1-3, FIG. 9D) after treatment with D-RNAi directed against β-catenin. In this figure, C is hybridized to a β-catenin probe, while D is hybridized to a GAPDH probe, to show that equivalent concentrations were loaded. Controls used include liposome alone and similar concentrations of perfectly matched sDNA-aRNA.

Figure 10:
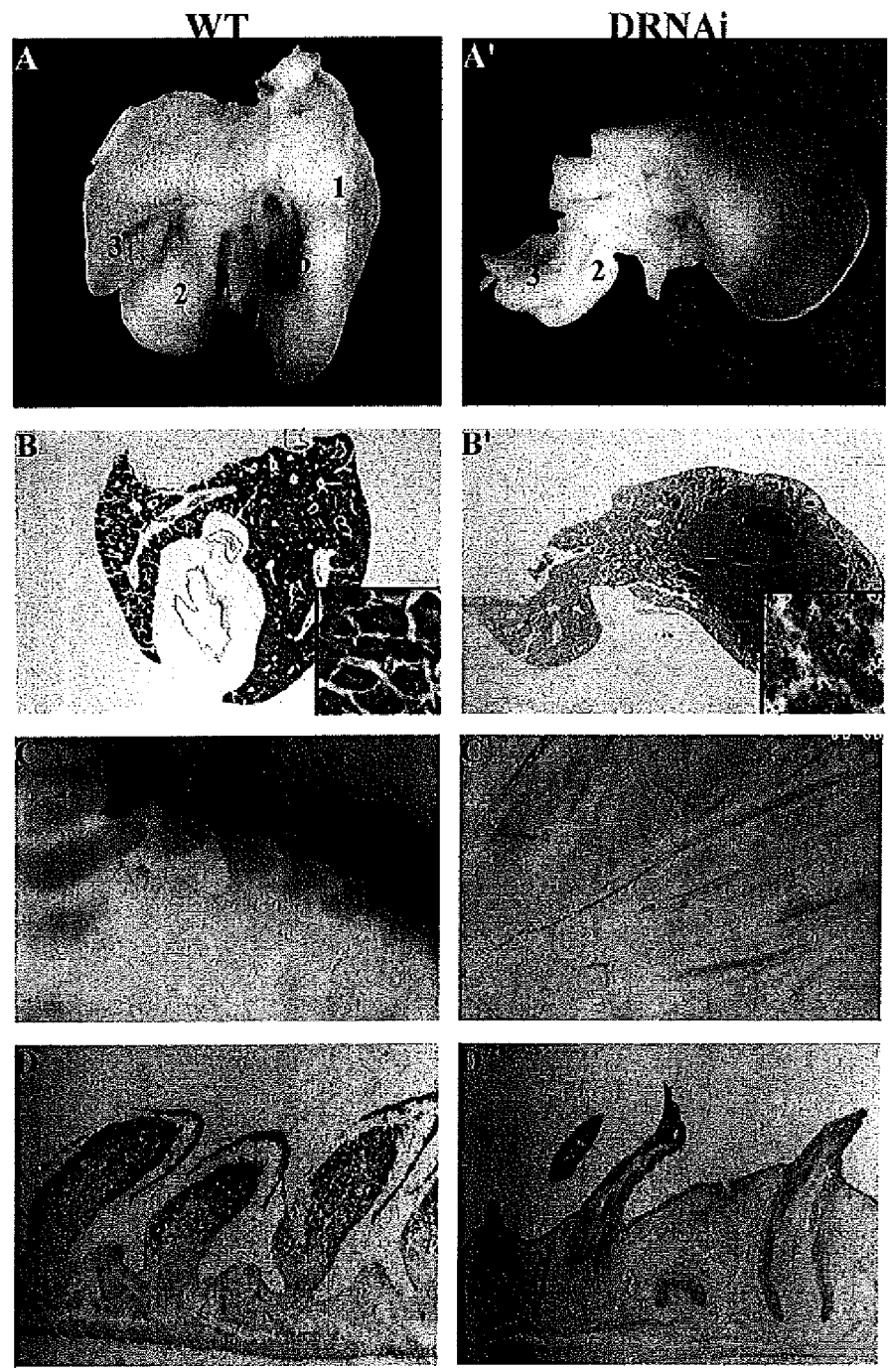
FIG. 10 illustrates the suppression of β-catenin gene expression in chicken liver (A' and B') and feather (C' and D' according to one embodiment of the present invention.

Livers after ten days of injection with sRNA-aDNA duplex showed an enlarged and engorged first lobe, but the size of the second and third lobes of the livers were dramatically decreased (FIG. 10A-A'). Histological sections of normal liver showed hepatic cords and sinusoidal space with few blood cells. In the β-catenin treated embryos, the general architecture of the hepatic cells in lobes 2 and 3 remained unchanged. However, in lobe 1 there are islands of abnormal regions. The endothelium development appears to be defective and blood is outside of the blood vessels. Abnormal types of hematopoietic cells are observed between the space of hepatocytes, particularly dominated by a population of small cells with round nuclei and scanty cytoplasm. In severely affected areas, hepatocytes were disrupted (FIG. 10B, B').

Since skin is exposed in the amniotic cavity and is most accessible to the nucleotides that leaked out, patches of skin that showed phenotypes were also observed. At embryonic day 13, skin should have formed elongated feather buds, with a primordial blood vessel running into its mesenchymal core. In the sRNA-aDNA β-catenin affected region, feather buds become engorged with blood, starting from the distal end of the feather tip (FIG. 10C, C'). The adjacent skin was normal (not shown), and works as a good control. Histological sections showed that the normal feather buds have continued their morphogenetic process with the epidermis invaginated to form the feather follicle walls, surrounding a mesenchymal core. In affected areas, the distal feather bud mesenchyme was full of engorged blood vessels and blood cells. Distal epidermis also detached from the feather mesenchyme, and proximal epidermis failed to invaginate to form follicles (FIG. 10D, D').

Example 9

Generation of bcl-2 RNA-DNA Probes

Following a RNA-PCR procedure similar to the Examples 1-4 and 5, four synthetic oligonucleotides were used in the generation of bcl-2 RNA-DNA duplexes as follows: sense T7-bcl2 primer (5'-dAAACGACGGC CAGTGAATTG TAATACGACT CACTATAGGC GGATGACTGA GTAC-CTGAAC CGGC-3') (SEQ ID. NO. 11) and anti-bc12 primer (5'-dCTTCTTCAGGCCAGGGAGGCATGG-3') (SEQ ID. NO. 12) for mRNA-cDNA hybrid (D-RNAi) probe preparation; T7-anti-bcl2 primer (5'-dAAACGACGGC CAGT-GAATTG TAATACGACT CACTATAGGC CTTCTTCAGG CCAGGGAGGC ATGG-3') (SEQ ID NO. 13) and sense bcl2 primer (5'-dGGATGACTGAGTACCTGAACCGGC-3') (SEQ ID NO. 14) for antisense RNA (sRNA)-cDNA hybrid (reverse D-RNAi) probe preparation. The design of the sequence-specific primers is based on the same principle used by PCR (50-60% G-C rich), while that of the promoter-linked primers however requires a higher G-C content (60-65%) working at the same annealing temperature as above sequence-specific primers due to their unmatched promoter regions. For example, new annealing temperature for the sequence-matched region of a promoter-linked primer is equal to $[2° C.\times(dA+dT)+3° C.\times(dC+dG)]\times5/6$, not including the promoter region. All primers were purified by polyacrylamide gel electrophoresis (PAGE) before use in RNA-PM reaction. The bcl-2 RNA-DNA hybrid probes so obtained were designed to target a highly conserved region of the bcl-2 gene (NCBI accession number M14745).

Example 10

Treatment of LNCaP Cancer Cells By Silencing bcl-2 Expression

LNCaP cells were obtained from the American Type Culture Collection (ATCC, Rockville, Md., and grown in RPMI 1640 medium supplemented with 10% fetal bovine serum with 100 µg/ml gentamycin at 37° C. under 10% $CO_2$. These cultured cells were treated with one dose of 100 nM 5α-anrostan-17β-ol-3-one to induce bcl-2 expression. For liposomal transfection of anti-bcl-2 probes, the probes (5 nM) in DOTAP liposome (Roche Biochemicals) were applied to a 60 mm culture dish which contained LNCaP cells at 15% confluency. After a 18-hour incubation, the cells took up about 60% of the probe-containing liposome. Uptake improved to 100% after 36 hours of incubation. The addition of α-amanitin was completed at the same time as the liposomal transfection. The apoptotic effect of phorbol-12-myristate-13-acetate (10 mM) was initiated at 12 hours after liposomal transfection. The mRNAs from the transfected LNCaP cells were isolated by poly-(dT) dextran columns (Qiagen, Santa Clarita, Calif.), fractionated on a 1% formaldehyde-agarose gel after a 36-hour incubation period, and transferred onto nylon membranes. After 48-hour transfection, genomic DNAs were isolated by an apoptotic DNA ladder kit (Roche Biochemicals) and assessed on a 2% agarose gel. Cell growth and morphology were examined by microscopy and cell counting, following known techniques. (See e.g., Lin et al., (1999) *Biochem. Biophys. Res. Commun.* 257, 187-192).

Example 11

Probe Preparation In Androgen-Treated LNCaP Cells

For the generation of RNA-DNA probes, an RNA-polymerase cycling reaction (RNA-PCR) procedure was modified to generate either sRNA-aDNA or cDNA-aRNA duplexes. Total RNAs (0.2 µg) from androgen-treated LNCaP cells were applied to a reaction (50 µl in total) on ice, comprising 5 µl of 10×RT&T buffer (400 mM Tris-HCl, pH 8.3 at 25° C., 400 mM NaCl, 80 mM $MgCl_2$, 2 M betaine, 100 mM DTT and 20 mM spermidine), 1 µM sequence-specific primer for reverse transcription, 1 µM promoter-linked primer for cDNA-doublestranding, 2 mM rNTPs, 2 mM dNTPs and RNase inhibitors (10 U). After *C. therm.*/Taq DNA polymerase mixture (4 U each) was added, the reaction was incubated at 52° C. for 3 min, 65° C. for 30 min, 94° C. for 3 min, 52° C. for 3 min and then 68° C. for 3 min. This formed a promoter-linked double-stranded cDNA for next step of transcriptional amplification up to 2000 fold/cycle. An in-vitro transcription reaction was performed by adding T7 RNA polymerase (160 U) and *C. therm.* polymerase (6 U) into above reaction. After one hour incubation at 37° C., the resulting mRNA transcripts were continuously reverse-transcribed into mRNA-cDNA duplexes at 52° C. for 3 min and then 65° C. for 30 min, so as to form sRNA-aDNA probes. The generation of sDNA-aRNA probes was the same procedure as aforementioned except using 1 µM sequence-specific primer for cDNA-doublestranding and 1 µM promoter-linked primer for reverse transcription. The RNA-PCR procedure can be reiterated to produce enough RNA-DNA probes for gene silencing analysis. For the preparation of double-stranded RNA probes, complementary RNA products were transcribed from both orientations of above promoter-linked double-stranded cDNAs and mixed together without reiterating reverse transcription activity. The quality of amplified probes were assessed on a 1% formaldehyde-agarose gel.

Example 12

Gene Silencing Using DNA-RNA Duplexes

An In Vitro Breast Cancer Model

As noted earlier, posttranscriptional gene silencing (PTGS) and RNA interference (RNAi) have been found capable of quelling specific gene activities in a variety of in vivo systems.

According to the invention provided herein, ectopic transfection of a sequence-specific DNA-RNA duplex (instead of a transgene dsDNA or dsRNA) is used to induce intracellular gene silencing in human cells. Although previous transgene/dsRNA transfection experiments showed that PTGS/RNAi effects are limited to plants and some simple animals, using the present invention, specific gene interference of β-catenin expression in human MCF-7 breast cancer cells using the DNA-RNA transfection has been successfully detected.

Normal human mammary granular cells do not express β-catenin protein, whereas neoplastic breast tissues from late-stage patients show a highly elevated level of this proliferation-stimulating oncoprotein. The malignancy and metastatic potentials of the breast cancer cells are also significantly increased after β-catenin expression. It is known in the art that over-expression of β-catenin protects malignant cancer cells from apoptosis and confers resistance to many anticancer drugs in vivo. To overcome such resistance, transcriptional knock down or knockout gene therapy may provide a counteract control for the expression of β-catenin.

Figure 12A:
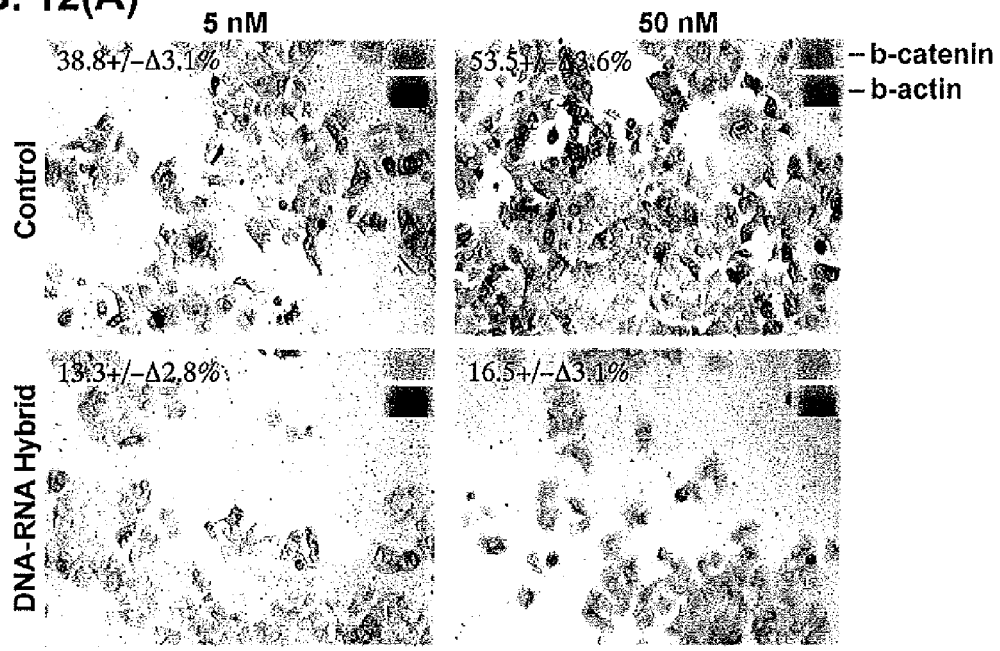
FIG. 12 is the in-cell results of Example 12 of the subject invention.

The potential utility of DNA-RNA transfection in preventing oncogene expression was therefore tested on β-catenin-expressing MCF-7 cells, expecting to reduce β-catenin protein amount and increase cancer cell susceptibility to apoptotic stimuli. Following our previous findings, MCF-7 cells were treated with different dosages of anti-β-catenin sense DNA-antisense RNA (DNA-RNA) probes (5 nM at an optimally effective concentration and 50 nM at a ten-fold high concentration). FIG. 12(a) shows the immunostaining results of expressed β-catenin protein in red ACE substrate color. At a 5 nM concentration of the DNA-RNA transfection (n=4), the expression rate was decreased from 38.8±3.1% (control) to 13.3±2.8% (transfected) cell population, indicating a 65.8% reduction. At a 50 nM concentration (n=5), the expression rate was decreased from 53.5±3.6% (control) to only 16.5±3.1% (transfected) cell population, indicating a 69.3% reduction.

The silencing of β-catenin expression also decreases the proliferation rate of cancer cells. At a 5 nM concentration of the DNA-RNA transfection (n=4), the density of cell population was decreased from average 112 (control) to 43 cell/$mm^3$ (transfected), indicating a 62.7% reduction. At a 50 nM concentration (n=5), the density of cell population was decreased from average 155 (control) to only 37 cell/$mm^3$ (transfected) cell population, indicating a 76.2% reduction. It is also noted that the cell morphology of all four sets is the same, without the debris of apoptotic bodies (interferon-caused cell death). Such findings suggest that the DNA-RNA transfection can successfully knock out average 67% of β-catenin oncogene expression and inhibit more than 62% cancer cell growth without the induction of cytotoxicity. Contrary to previous dsRNA reports, dsRNA transfection usually causes a very significant interferon-induced cytotoxicity at the concentrations more than 10 nM.

Figure 12B:
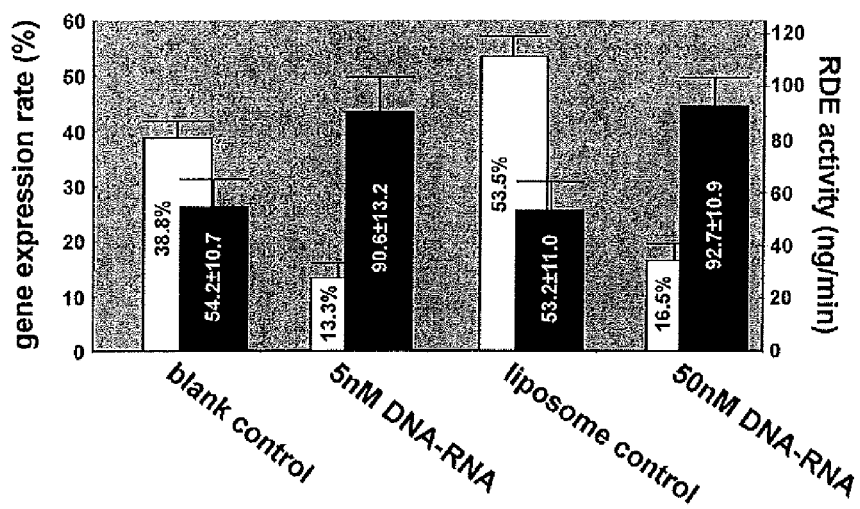

The increase of RNA-directed endoribonuclease (RDE) activity is also detected after DNA-RNA transfections. As noted earlier, the RDE is required for the onset of PTGS/RNAi phenomena in many in cell and in vivo systems. The activity of RDE is measured by adding 2 µl cell extracts into 2 µl of 1 kb dsRNA preparations for 10 min at 25° C. Since the dsRNA is labeled by [$^{33}$P]-CTP (>3000 Ci/mM, Amersham International), the degradation rate can be easily observed by 1% agarose gel electrophoresis, blot transferring and then film exposure. The bar chart of FIG. 12(b) shows the RDE activity in black bars and the gene silencing rate in white bars. At a 5 nM concentration of the DNA-RNA transfection (n=4), the RDE activity was promoted from 54.2 (control) to 90.6 ng/min (transfected), indicating a 167% increase rate. At a 50 nM concentration (n=5), the RDE activity was promoted from 53.2 (control) to 92.7 ng/min (transfected), indicating a 174% increase rate. This data suggests that the DNA-RNA transfection induce a gene-specific silencing effect through the PTGS/RNAi phenomena.

There are three major effects of PTGS, i.e., initiation, spreading and maintenance, all of which are also found in many inheritable RNAi phenomena. The initiation indicates that the onset of PTGS/RNAi takes a relatively long period of time (1~3 days) to develop enough small RNA or short interfering RNA (siRNA) for specific gene knockout. With traditional antisense transfection processes, it only takes several hours to reach the same gene silencing results but with much higher dosages and higher cytotoxicity. Also, unlike the short-term effectiveness of traditional antisense transfections, the PTGS/RNAi effects may spread from a transfected cell to neighboring cells and can be maintained for a very long time (weeks to lifetime) in a mother cell as well as its daughter cells (Grant (1999) supra). Based on these features, a more efficient and reliable gene therapy is expected.

Preparation of DNA-RNA Duplexes For β-Catenin Knockdown

Few fixed and permeabilized MCF-7 cells were applied to a reaction (20 μl) on ice, comprising 2 μl of 10×RT&T buffer (400 mM Tris-HCl, pH 8.3 at 25° C., 350 mM KCl, 80 mM MgCl$_2$, and 100 mM DTE), 1 μM β-catenin-antisense promoter-linked primer 5'-dAAACGACGGC CAGTGAATTG TAATACGACT CACTATAGGC GCTCTGAAGA CAGTCTGTCG TGATGG-3' (SEQ ID.15), 1 μM β-catenin-sense primer 5'-dATGGCAACCC AAGCTGACTT GATC-3' (SEQ ID.16), ribonucleotide triphosphates (4 mM each for ATP GTP, CTP and UTP), deoxyribonucleotide triphosphates (4 mM each for dATP dGTP, dCTP and dTTP), and RNase inhibitors (10 U). After C. therm./Taq DNA polymerase mixture (4 U) was added, the reaction was incubated at 52° C. for 3 min, 65° C. for 30 min, 94° C. for 3 min, 52° C. for 3 min and then 68° C. for 3 min. A transcription reaction was prepared by adding T7 RNA polymerase (200 U) and C. therm. polymerase (6 U) mixture into above reaction. After three-hour incubation at 37° C., the resulting antisense RNA transcripts were continuously reverse-transcribed into DNA-RNA duplexes at 52° C. for 3 min and then 65° C. for 30 min. The quality of amplified DNA-RNA products can be assessed on a 1% formaldehyde-agarose gel (Lin (1999) supra). The β-catenin DNA-RNA probe (10 μg) so obtained was designed to target a highly conserved region of the human β-catenin gene (NCBI accession number X87838). The resulting product was purified by microcon-30 filter, dissolved in 75 μl of Hepes buffer (pH 7.4).

In-Cell Transfection And Gene Silencing In MCF-7 Breast Cancer Cells

The above β-catenin DNA-RNA probe (10 μg) in 75 μl of Hepes buffer (pH 7.4) was mixed with 50 μl of DOTAP liposome (1 mg/ml, Roche Biochemicals) on ice for 30 min before applied to 60 mm (2 ml) diameter culture dishes which contain 50% confluency of MCF-7 cancerous cells. The MCF-7 cells were grown in MEM medium with 10% bovine serum. After 72 hr incubation, the gene expression of β-catenin protein was shown by immuno-histochemical staining with 50 μg/ml anti-β-catenin antibodies (Santa Cruz BioLab) and found to be reduced more than 66~70% in the DNA-RNA set while the blank and liposomal control sets have no significant gene silencing effects (FIG. 12(a)). The RNA-directed endoribonuclease (RDE) activity of the DNA-RNA transfection set was also detected to show a 167~2174.2% increase following the reduction of β-catenin expression (FIG. 12(b)). Such increase of RDE activity reflects a high RNAi effect induced by the DNA-RNA transfection. Because the over-expression of β-catenin oncogene has been known to increase the malignancy and metastasis of human breast cancers in vivo, the above findings could provide an effective therapy and/or anti-cancer drug for the prevention of cancer invasion and progression.

Example 13

Gene Silencing Using DNA-RNA Duplexes

An Ex Vivo Model Targeting HIV-1 Genome In CD4$^+$ T Lymphocytes

The foregoing establishes that the novel DNA-RNA duplexes of the present invention can be used in a novel strategy to knock out targeted gene expression in vitro. As discussed below, the novel DNA-RNA strategy of the invention is also effective in knocking out gene expression ex vivo.

As illustrated in the examples below, the methods and compositions of the invention are effective in knocking out exogenous viral gene expression ex viva in a CD4$^+$ T lymphocyte extract model. For molecules, HIV-1 genome from +2113 to +2453 bases was targeted because it has a critical role in viral replication activity, and for cells, CD4$^+$ T lymphocyte was selected because it is a cell often targeted by HIV-1 infection. The HIV-1 is known to be the infectious pathogen of AIDS diseases. To a world-wide estimation till year 2000, more than 36 million people are currently infected by HIV-1, and this number is increased by at least 2 million per year. About four million AIDS patients have deceased this year due to the lack of an effective and stable long-term treatment for eradicating the malignancy of this virus.

The high mutation rate of HIV genome gradually generates more and more unexpected resistance to traditional HAART cocktail therapy, exacerbating the prevalence of this disease. Such dramatic increase of new mutant viruses as well as their carriers will soon become a very heavy finance burden for all health care and related disease prevention programs. However, although the high mutation rate of HIV-1 genome enable it to escape the traditional chemotherapy, it is impossible for HIV to change the whole targeted sequence, which can be several hundred bases homologous to our DNA-RNA probe. Because the cosuppression effect of RNAi phenomenon to all homologous transcripts, the HIV genes is impossible to evade the silencing effects of DNA-RNA transfection by its mutations. It is very promising that the DNA-RNA transfection could become a powerful antiviral drug or vaccine for the prevention, or therapy, of viral infections.

Figure 13A:
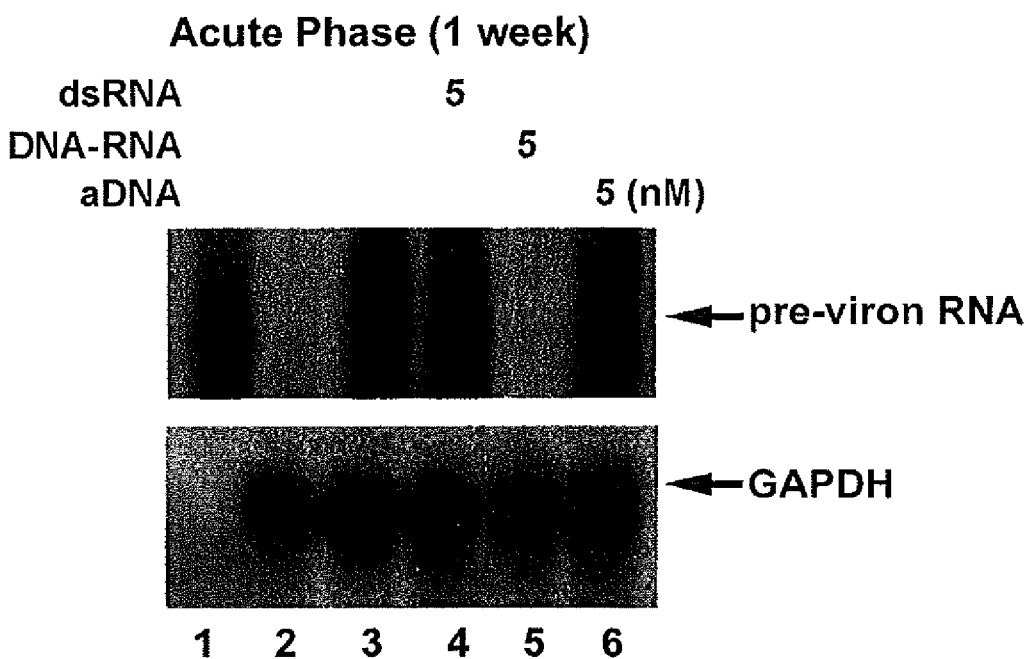
FIG. 13 is the ex-vivo results of Example 13 of the subject invention.
Figure 13B:
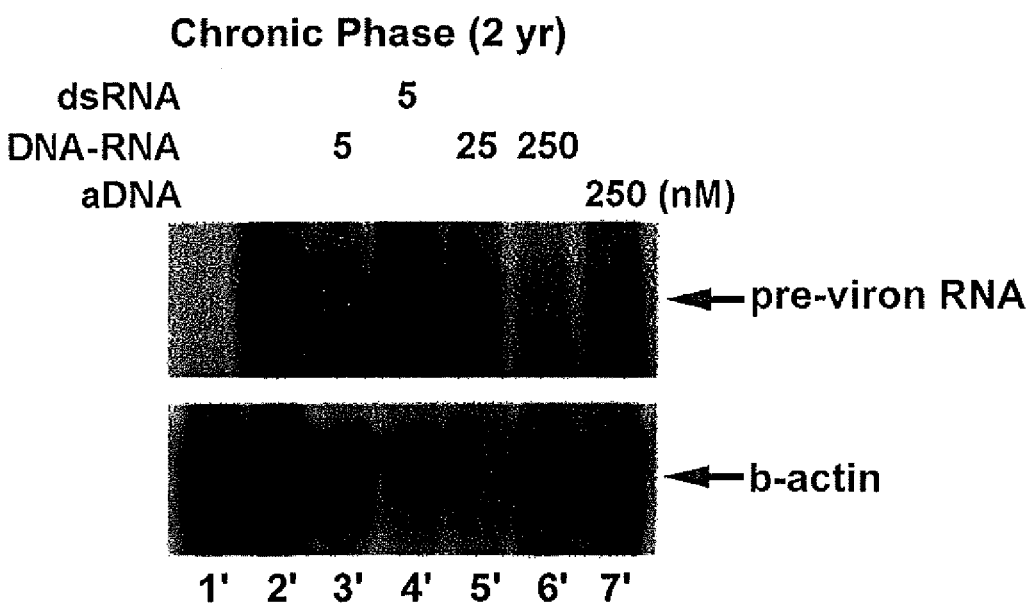

FIG. 13(a) shows the gene silencing effect of anti-HIV-1 DNA-RNA transfections (n=3 for each set) in acute phase AIDS patient T lymphocyte extracts, while FIG. 13(b) shows the same effect in chronic phase AIDS patient T lymphocyte extracts. The lane 1 of FIG. 13(a) is pure HIV-1 genome to indicate the size location on an electrophoresis gel. The lane 2 of FIG. 13(a) and lane 1' of FIG. 13(b) are T lymphocyte RNA extract samples from normal non-infected persons as negative control. The lane 3 of FIG. 13(a) and lane 2' of FIG. 13(b) are extract samples from HIV-1-infected patients as positive control. In the acute phase (one-week infection), the treatment of 5 nM DNA-RNA transfection completely knocks out entire viral gene expression, while those of 5 nM dsRNA and traditional antisense DNA transfection have very minor effects. In the chronic phase (two-year infection), the treatment of 25 nM DNA-RNA transfection knocks out 55.8% viral gene expression, while the transfections of 25 nM dsRNA and 250 nM traditional antisense DNA have no specific effects. When the DNA-RNA concentration is increased to 250 nM (FIG. 13(b), lane 6'), the transfection knocks out 61.3% viral gene expression without the induction of cytotoxicity. The expression of cellular house-keeping genes, GAPDH and β-actin, is normal and shows no interferon-induced non-specific RNA degradation in most of lanes, except the dsRNA treatments. These findings have directed to an immediate therapy potential for AIDS in both acute and chronic infections.

As discussed above, the experimental results establish that DNA-RNA probes potentially inhibit β-catenin expression in the MCF-7 cancer cells and also prevent HIV-1 viral activity in the CD4+ T lymphocytes. Thus, the results show that using an DNA-RNA duplex provides a powerful new strategy for gene therapy. At the highest dosage used in the experiments here (FIGS. 12 and 13), the DNA-RNA transfection did not cause interferon-induced cytotoxicity as previous reports in dsRNA transfections. This even underscores the fact that the DNA-RNA comprising compositions of the instant invention are effective even at low dosages. The results also indicate that this invention is effective in knocking out the targeted gene expression over a relatively long period of time. Further, it was observed that non-targeted cells appear to be normal, which implies that the compositions herein possess no overt toxicity. Thus, the invention offers the advantages of low dosage, stability, long term effectiveness, and lack of overt toxicity.

Preparation of DNA-RNA Duplexe For Ex-Vivo Transduction And Gene Silencing of HIV-1 Replication A part of the human immunodeficiency virus type 1 (HIV-1) genome sequence (NCBI accession number U21135) from +2113 to +2453 bases was cloned into pCR2.1 plasmid vector (Invitrogen) for the preparation of a DNA-RNA probe homologous to HIV-1 gag-pro-pol genes. Since the pCR2.1 plasmid contains a T7 promoter in front of its antisense clone site, the RNA portion of the DNA-RNA duplex construct can be directly amplified in an in-nitro transcription reaction (20 μl), comprising 2 μl of 10×RT&T buffer (400 mM Tris-HCl, pH 8.3 at 25° C., 300 mM KCl, 80 mM $MgCl_2$, 2M betaine, 100 mM DTE and 20 mM spermidine), rNTPs (4 mM each for ATP GTP, CTP and UTP), T7 RNA polymerase (200 U), RNase inhibitors (10 U) and the above pCR2.1 plasmid (10 μg). The reaction was performed at 37° C. for two hours and then reverse transcription (40 μl) was continuously performed in the same tube by adding 2 μl of 10×RT&T buffer, dNTPs (4 mM each for dGTP, dCTP, dTTP and 2 mM each for dATP and dITP), MMLV reverse transcriptase (30 U) and 1 μM sense primer 5'-dGGATGICIGI CICCTTGTTG GTCC-3' (SEQ ID.17). The reaction was further incubated at 37° C. for two hours, so as to provide about 30 μg DNA-RNA probes for transfection.

The above HIV-1 DNA-RNA probe (10 μg) was dissolved in 200 mM calcium phosphate and directly applied to 2 ml culture flask contain 50% confluency of CD4+ T lymphocytes. The T lymphocytes were extracted from patients and can be grown in human serum extracts with 100 μg/ml interleukin 2 (IL-2) for two weeks. After 96 hr incubation, the gene activity of HIV-1 genome was measured by Northern blotting and found to be almost completely shut down in the DNA-RNA transfection set (FIG. 13(a), lane 5; and FIG. 13(b), lanes 3', 5' & 6'). The blank control (FIG. 13(a), lane 2; and FIG. 13(b), lane 1') and other construct transfection (FIG. 13(a), lanes 4 & 6; and FIG. 13(b), lanes 4' & 7') sets had no significant gene silencing effects. Unlike dsRNA treatment, the transfection of high concentrated DNA-RNA probes (250 nM; FIG. 13(b), lane 6') did not cause any interferon-induced killing effects, because the house-keeping gene β-actin is normally expressed in all sets of transfected cells as well as non-transfected HIV-1-negative control (FIG. 13(a), lane 2; and FIG. 13(b), lane 1') and -positive (FIG. 13(a), lane 3; and FIG. 13(b), lane 2') control sets. The FIG. 13(a) showed the acute transfection results of HIV-1 DNA-RNA probes in one-week-infection patients, while the FIG. 13(b) showed the chronic transfection results of HIV-1 DNA-RNA probes in two-year-infection patients. Because the Northern blot method is able to detect HIV-1 gene transcript at the nano-gram level, the above strong viral gene silencing effect actually demonstrates a very promising pharmaceutical and therapeutical use of this DNA-RNA duplex construct as antiviral drugs and/or vaccines.

Example 14

Gene Silencing Using DNA-RNA Duplexes

An In Vivo Model For Interfering Tyrosinase Gene Expression In Mouse Skin Hairs

The foregoing establishes that the novel DNA-RNA duplexes of the present invention can be used in a novel strategy to knock out targeted gene expression in vitro as well as ex vivo. As discussed below, the novel DNA-RNA strategy of the invention is also effective in knocking out gene expression in vivo.

Figure 14:
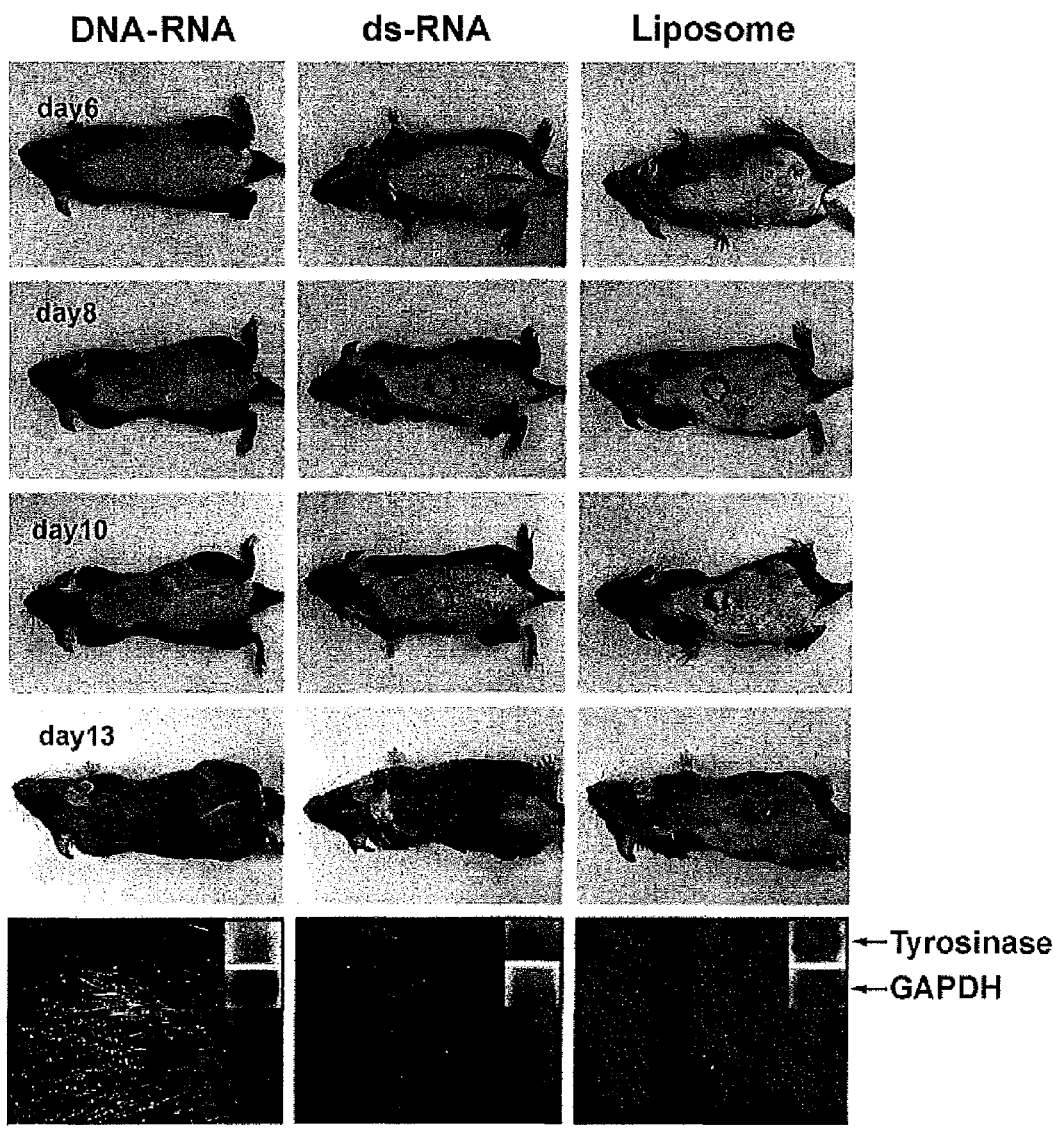
FIG. 14 is the in-vivo result of Example 14 of the subject invention.

As illustrated in the examples below, the methods and compositions of the invention are effective in knocking out specific gene expression in vivo in a mouse skin hair model. As shown in FIG. 14, albino (white) skin hairs of melanin-knockout mice were created by four times of intra-cutaneous (i.c.) transduction of about 50 nM DNA-RNA per day against tyrosinase (tyr; NCBI accession number M26729) gene transcripts. The expression of melanin (black pigment) in skins and hairs has been blocked due to a loss of its intermediate generation by the tyrosinase knockout. Contrarily, the control and double-stranded RNA (dsRNA) transfected mice presented normal skin color (black), indicating that the loss of melanin is specific to RNAi silencing effect induced by the DNA-RNA transfection. Moreover, Northern blotting showed a 76.1±5.3% reduction of tyr gene expression after the DNA-RNA transfection, while minor non-specific degradation of common gene transcripts (such as GAPDH) was detected in the dsRNA transfected skins.

As discussed here, the experimental results establish that DNA-RNA probes potentially inhibit tyrosinase gene expression in the transfected mice skins and therefore prevent the production of melanin (black pigment) in hairs. Thus, the results show that using a DNA-RNA duplex provides a powerful new strategy for gene therapy, especially to melanoma. At the same dosage (200 nM in total), the DNA-RNA transfection did not cause any cytotoxicity effect, while the dsRNA transfections induced detectable non-specific mRNA degradation as previous reports (Stark (1998) supra, and Elbashir (2001) supra). This even underscores the fact that the DNA-RNA comprising compositions of the instant invention are effective even under in vivo systems without the side-effects of dsRNA. The results also indicate that this invention is effective in knocking out the targeted gene expression over a relatively long period of time because the hair regrowth requires at least ten-day recovery. Further, it was observed that non-targeted skin hairs appear to be normal, which implies that the compositions herein possess high specificity and no overt toxicity. Thus, the invention offers the advantages of low in-viuo dosage, high stability, long-term effectiveness, and lack of overt toxicity.

Preparation of DNA-RNA Duplexes For In-Vivo Transduction And Gene Silencing In Mouse Partial Mus musculus tyrosinase (tyr) sense DNA (sDNA) sequence (SEQ ID.18) purchased from a core facility (Invitrogen) was synthesized by an oilgonucleotide synthesizer machine. The complementary antisense RNA (aRNA) sequence (SEQ ID.19) was transcribed from a tyr-inserted RCAS-viral vector which is a genetically engineered retrovirus capable of delivering a gene insert of interest or its related components into a host cell genome and expressing the gene products, such as RNA, peptide and protein in the cell, The synthesized sDNA was boiled at 94° C., 10 min in diethyl pyrocarbonate (DEPC)-added H2O (~pH 5.5). Hybridization of the tyr sDNA and aRNA was accomplished by incubation of 200 µg of each sequence in a 20 mM Hepes buffer (pH 6.5) at 68° C. for over 10 min and then gradually cooling from 50° C. to 10° C. over a period of 30 min. The final DNA-RNA hybrid product was stored in a −80 freezer before used.

The dorsal hairs of one-month-old W-9 black mice were stripped by wax. Four intra-cutaneous injections of the tyr DNA-RNA (25 µg for each injection) were applied by a 24 hr interval fashion for each injection. After a thirteen-day hair regrowth period, white hairs were observed only in the injected area of the DNA-RNA transfected mice, while those of the dsRNA transfected and blank control mice showed normal black colored hairs. Northern analysis of the tyr gene expression indicated a 76.1±5.3% reduction in the transfected skins of the DNA-RNA treated mice, but no such gene silencing effect was found in the dsRNA transfected and blank control mice.

Example 15

The DNA-RNA duplex molecule can be used for a wide variety of applications in relation to inducing RNA interference or altering the characteristic of the cell. In one example, the DNA-RNA duplex molecule may serve as a therapeutic agent to effectuate a therapeutically desirable outcome in physiological conditions. As seen in examples 1-3, the DNA-RNA may be used to inhibit proliferation of cancer cells, fight viral infection, and alter pigmentation of cells. Although the examples above used a single species of DNA-RNA duplex molecule for each condition, it is contemplated that multiple species of DNA-RNA probes, as a cocktail, may be used to combat multi-factorial disease condition. Preferably, the cocktail may include at least two to ten species of DNA-RNA hybrids each having a different nucleic acid sequence from the other species in the cocktail.

In order for the DNA-RNA duplex to be effectively delivered into the cell in vivo as a therapeutic agent, it is also contemplated that DNA-RNA duplex molecules or multiple species of the molecule will be formulated for effective delivery. Examples of formulations may include formulations in saline, liposomes such as DOTAP and co-lipids, polymers such as polyethylene glycol, polyvinyl pyrrolidone, poly vinyl alcohol, and other transfection inducing polymers and agents. Delivery may be via intra-muscular, intra-dermal, intra-tumor, intraperitoneal, systemic injections with or without electroporation. The formulations may also include targeting ligands such as antibodies specific to a particular cell to form, for example, immunoliposomes. Preferably, the therapeutic formulation of the DNA-RNA duplex molecule would be contained in an article of manufacture such as a kit, bottle, or tube with a label indicating its use. The label may be affixed to the article or may be separate such as an instruction sheet or manual.

In certain situations, it is also contemplated that the DNA-RNA would not need to be delivered into the body. For example, ex uivo inhibition of viral replication such as disclosed in Example 2 may be useful. The HIV patients may have their own $CD4^+$, or any other blood, marrow, or precursor cells, removed and treated and transplanted back into their system. This eliminates any immune type rejection of the transplanted cells that would have occurred if the cells were from a different individual.

In the area of specialized individual medicine, the DNA-RNA duplex molecule may also be used to treat individualized conditions. For example, a differential expression analysis using microarray or subtractive hybridization technology may be used to determine aberrant gene expression in an individual having the condition to be treated. Over-expressing genes, such as seen in cancer cells over-expressing β-catenin, may then be knock out or down by the generating DNA-RNA duplex molecules directed toward those genes. A kit may be provided to the treating physician for performing the subtractive hybridization and using the over-expressed genes remaining from the subtraction as templates for DNA-RNA interference.

In another example, gene function may be analyzed for unknown or known genes by impairing its expression using the DNA-RNA duplex molecule just described. As genes are identified from the Human Genome Project, DNA-RNA duplex molecules may be generated and transfected into cells to observe the effect of the impairment of expression in the cell. As such, the function of the gene impaired may be deduced. The DNA-RNA duplex molecule agents may be introduced into the cell by a number of different methods such as nuclear micro-injection, electroporation, transfection by liposomes, calcium phosphate, dextran sulfates, or polymers.

In one specific embodiment, the method of the present invention comprises the steps of: a) providing: i) a substrate expressing a targeted gene, and ii) a composition comprising a DNA-RNA duplex agent capable of silencing the expression of the targeted gene in the substrate; b) treating the substrate with the composition under conditions such that gene expression in the substrate is inhibited. The substrate can express the targeted gene in vitro or in vivo.

In another specific embodiment, the method for inducing RNAi-mediated gene silencing effects using DNA-RNA duplex constructs comprises the steps of:
  a. providing a plurality of DNA sequences, wherein said DNA sequences are either homologous or complementary to a or a plurality of targeted intracellular messenger RNA sequences;
  b. contacting said DNA sequences to a plurality of RNA sequences to form a plurality of DNA-RNA duplexes, wherein said RNA sequences are complementary to said DNA and intracellular messenger RNA sequences; and
  c. transducing said DNA-RNA duplexes into a cell or a plurality of cells which are sensitive to RNA interference effects; and so as to provide a specific gene silencing effect to the targeted gene(s) within said cells.

The said DNA sequences may be synthesized by a machine such as an oligonucleotide synthesizer, a thermocycler, an isothermal incubator, or any other suitable machine for synthesizing DNA sequences. Preferably, the said DNA sequences are form from one or a plurality of nucleic acid templates using enzymatic reaction such as reverse transcription, polymerase chain reaction, nucleic acid sequence based amplification, and RNA-polymerase cycling reaction. The templates may be single or double stranded, linear of circular structures. For purpose of gene silencing, the said DNA sequences may be completely or partially homologous to said intracellular messenger RNA sequences that are targeted.

Similarly, the said RNA sequences may be synthesized by a machine such as an oligonucleotide synthesizer, thermocycler or isothermal incubator. Alternatively, the RNA, may be generated from one or a plurality of nucleic acid templates by enzymatic methods such as in-vitro transcription, aRNA amplification, nucleic acid sequence based amplification (NASBA), and RNA-polymerase cycling reaction (RNA-PCR). The templates may also be single- or double-stranded, linear or circular in structures. The said RNA sequences may be completely or partially complementary to said DNA sequences.

Synthesis of the RNA and DNA molecules may also be performed separately and allowed to anneal or hybridize to form duplex sequences. Preferably the hybridization, occurs in a Hepes-containing buffer at about 68° C. for more than 10 minutes. The Hepes-containing buffer is preferably a 20 mM HEPES solution.

In a further embodiment, a kit is provided for inducing gene silencing effects using DNA-RNA duplex constructs. The kit comprises the following components:
  a. a plurality of DNA-RNA duplex constructs, wherein the DNA portion of said DNA-RNA duplex constructs are homologous to a or a plurality of targeted intracellular messenger RNA sequences; and
  b. a plurality of transfection reagents, wherein said transfection reagents can deliver said DNA-RNA duplex constructs into a plurality of targeted cells; and so as to provide a specific gene silencing effect to the targeted messenger RNAs within said cells.

Example 16

Another embodiment of the present invention is the modification of the RNA-Polymerase Chain Reaction (RNA-PCR) as disclosed in U.S. Pat. No. 6,197,554 having common inventors in this application. The modification being the use of primers having sequence specific sequences and the RNA promoter sequences to amplify and generate DNA-RNA duplex molecules.

Briefly, the elevated thermocycling temperature of the RNA-PCR method prevents rapid degradation of short-lived RNAs and further reduces the secondary structure of RNAs to increase the accessibility of enzyme interactions and the production of more complete desired RNAs. The procedure uses thermostable enzymes, including Tth-like polymerases with reverse transcriptase activity. The use of proofreading RNA polymerases for amplification not only provides higher fidelity but also eliminates preferential amplification of abundant RNA species. Additionally, rapid and simple cell fixation and permeabilization steps inhibit any alterations in gene expression during specimen handling or genomic contamination. (See, Embleton et al., (1992) *Nucl Acids Res.* 20, 3831-3837).

In yet another embodiment, the method for generating DNA-RNA duplexes for gene silencing comprises the steps of:
  a) providing: i) a solution comprising a nucleic acid template, ii) one or more primers sufficiently complementary to the sense conformation of the nucleic acid template, and iii) one or more promoter-linked primers sufficiently complementary to the antisense conformation of the nucleic acid template, and having an RNA promoter;
  b) treating the nucleic acid template with one or more primers under conditions such that a first DNA strand is synthesized;
  c) treating the first DNA strand with one or more promoter-linked primers under conditions such that a promoter-linked double-stranded nucleic acid is synthesized;
  d) treating the promoter-linked double-stranded nucleic acid under conditions such that essentially RNA fragments are synthesized; and
  e) treating RNA fragments with one or more primers under conditions such that a DNA-RNA duplexes are synthesized.

Steps b) through e) of the above method are preferably repeated for a sufficient number of cycles to obtain a desired amount of amplified hybrid duplex product. Step b), for example, may include heating the solution at a temperature above 90° C. to provide denatured nucleic acids. Step c), for example may include treating the first DNA strand with one or more promoter-linked primers at a temperature ranging from about 37° C. to about 72° C. in the presence of a plurality of polymerases. Examples of the polymerases include DNA-dependent DNA polymerases, RNA-dependent DNA polymerases, RNA polymerases, Taq-like DNA polymerase, Tth-like DNA polymerase, *C. therm.* polymerase, viral replicases, and combinations thereof. The viral replicases can be selected from the group consisting of Avian myeloblastosis virus (AMV) reverse transcriptase and Moloney murine leukemia virus (MMLV) reverse transcriptase, Bromo mosaic virus (BMV) replicase and derivatives of reverse transcriptases that do not have RNase H activity. Step d) may include treating the promoter-linked double-stranded nucleic acid with an enzyme having transcriptase activity at about 37° C. such as T3 RNA polymerase, T7 RNA polymerase, SP6 RNA polymerase, and M13 RNA polymerase. Step d) may also include treating the promoter-linked double-stranded nucleic acid with viral replicases such as AMV reverse transcriptase, MMLV reverse transcriptase, BMV replicase and derivatives of reverse transcriptases that do not have RNase H activity.

In another embodiment, the method of improved reverse transcription-polymerase cycling reaction (RT-PCR or RNA-PCR) which amplifies a specific DNA-RNA duplex construct for transducing biological gene silencing effects comprises the steps of
  a. providing a plurality of nucleic acid sequences as an amplifiable gene template for following reactions;
  b. denaturing and contacting said nucleic acid template with a plurality of primers and a plurality of promoter-linked primers, wherein said primers and promoter-linked primers are respectively complementary to the sense and antisense sequence conformation of said nucleic acid template;
  c. permitting extension of said primers and promoter-linked primers to form a plurality of promoter-linked double-stranded nucleic acid sequences, wherein said promoter-linked double-stranded nucleic acid sequences are formed by either DNA-directed or RNA-directed DNA and/or RNA polymerases or the combination thereof;
  d. permitting transcription of said promoter-linked double-stranded nucleic acid sequences to form a plurality of amplified RNA fragments, wherein said amplified RNA fragments are generated by extension of RNA polymerase activity through the promoter region of said promoter-linked double-stranded DNAs; and e. contacting said amplified RNA fragments with said primer to form a plurality of DNA-RNA hybrid duplexes, wherein said DNA-RNA hybrid duplexes are formed by reverse transcription of said amplified RNA fragments with the extension of said primer; so as to provide amplified DNA-RNA hybrid duplexes ready for inducing RNAi-related gene silencing effects.

To increase the yield of DNA-RNA hybrid duplexes, steps (b) through (e) may be repeated at least one time. Furthermore, it may be preferable to have a plurality of nucleotide analogs into the DNA part of said amplified DNA-RNA duplexes in the step (e) to increase the onset of gene silencing effects. The nucleotide analogs by be generated by treatment with deaminase or chemical treatments such as using acidic solutions. With respect to the denaturing step in step b), it is preferred to use temperature at a range from about 90° C. to about 100° C., while the enzyme activities are preferably performed at temperature ranging from 37° C. to about 70° C.

REFERENCES

The following references are hereby incorporated by reference as if fully set forth herein:

1. Bahramian et. al., *Mol. Cell. Biology* 19, 274-283 (1999).
2. Bateman J R and Wu C T. (2007) *Bioessays* 29, 382-385.
3. Berchem, G. J., Bosseler, M., Sugars, L. Y., Voeller, H, J., Zeitlin, S., and Gelmann, E. P. (1995) *Cancer Res.* 55, 735-738.
4. Basher, J. M. and Labouesse, M., *Nature Cell Biology* 2: 31-36 (2000).
5. Chamberlin et al., *Nature* 228, 227-231 (1970).
6. Cogoni, C. and Macino, G. (1999) *Nature* 399, 166-169.
7. Colombel, M., Symmans, F., Gil, S., O'Toole, K. M., Chopin, D., Benson, M., Olsson, C A., Korsmeyer, S., Buttyan, R. (1993) *Am. J. Pathol.* 143, 390-400.
8. Compton, J., "Nucleic acid sequence-based amplification", *Nature* 350, 91-92 (1991).
9. Elbashir et. al., *Nature* 411, 494-498 (2001).
10. Embleton et al., *Nucl. Acids Res,* 20, 3831-3837 (1992).
11. Fire, A., Xu, S., Montgomery, M. K., Kostas, S. A., Driver, S. E., and Mello, C. C., *Nature* 391, 806-811 (1998).
12. Grant S., "Dissecting the mechanisms of posttranscriptional gene silencing: divide and conquer", *Cell* 96, 303-306 (1999).
13. Grimm D, Streetz K L, Jopling C L, Storm T A, Pandey K, Davis C R, Marion P, Salazar F, Kay M A, *Nature* 441, 537-541 (2006).
14. Grishok, A., Tabara, H., and Mello, C. C. (2000) Science 287, 2494-2497.
15. Hannoush et. al., *J. Am. Chem. Soc.* 123, 12368-12374 (2001).
16. Kacian et al., *Proc. Natl. Acad. Sci. USA* 69, 3038-3044 (1972).
17. Kennerdell, J. R. and Carthew, R. M., *Cell* 95, 1017-1026 (1998).
18. Ketting, R. F., Haverkamp, T. H., van Luenen, H. G., and Plasterk, R. H. (1999) *Cell* 99, 133-141.
19. Kwoh et al., *Proc. Natl. Acad. Sci. USA* 86, 1173-1177 (1989).
20. O'Donnell K A and Boeke J D. (2007) *Cell* 129, 37-44.
21. Shi-Lung Lin, Cheng-Ming Chuong, Randall B. Widelitz and Shao-Yao Ying, "In vivo analysis of cancerous gene expression by RNA-polymerase chain reaction", *Nucleic Acid Res.* 27, 4585-4589 (1999).
22. Shi-Lung Lin, Cheng-Ming Chuong and Shao-Yao Ying, "A novel mRNA-cDNA interference phenomenon for silencing bcl-2 expression in human LNCaP cells", *Biochem. Biophys. Res. Commun.* 281, 639-644 (2001).
23. Shi-Lung Lin and Shao-Yao Ying, "D-RNAi is a novel defense system against cancers and viral infections", *Current Cancer Drug Targets* 1, 241-247 (2001).
24. Shi-Lung Lin and Shao-Yao Ying; "Combinational therapy for HIV-1 eradication and vaccination". *Intrn'l J. Oncol.* 24, 81-88 (2004).
25. Shi-Lung Lin and Ying SY; "Novel RNAi therapy—Intron-derived microRNA drugs". *Drug Design Reviews* 1, 247-255 (2004).
26. McConkey, D. J., Greene, G., and Pettaway, C. A. (1996) *Cancer Res.* 56, 5594-5599.
27. Misquitta, L. and Paterson, B. M. (1999) *Proc. Natl. Acad. Sci. USA* 96, 1451-1456.
28. Myers and Gelfand, *Biochemistry* 30, 7662-7666 (1991).
29. Pal-Bhadra, M., Bhadra, U., and Birchler, J. A. (1999) *Cell* 99, 35-46.
30. Raffo, A. J., Perlman, H., Chen, M. W., Day, M. L., Streitman, J. S., and Buttyan, R. (1995) *Cancer Res.* 55, 4438-4445.
31. Sambrook et. al., "Molecular Cloning, $2^{nd}$ Ed.", Cold Spring Harbor Laboratory Press, pp 8.11-8.19 and pp 7.39-7.52 (1989).
32. Scott W. Knight and Brenda L. Bass, *Science* 293, 2269-2271 (2001).
33. Sledz C A, Holko M, de Veer M J, Silverman R H, Williams B R. *Nat Cell Biol.* 5, 834-839 (2003).
34. Smardon, A., Spoerke, J. M., Stacey, S. C., Klein, M. E., Mackin, N., and Maine, E. M. (2000) *Curr. Biol.* 10, 169-171.
35. Stark et. al., "How cells respond to interferons", *Annu. Rev, Biochem.* 67, 227-264 (1998).
36. Tabara, H., Sarkissian, M., Kelly, W. G., Fleenor, J., Grishok, A., and Timmons, L. (1999) *Cell* 99, 123-132.
37. Wargelius, A., Ellingsen, S., and Fjose, A. (1999) *Biochem. Biophys. Res. Commun.* 263, 156-161.
38. Wianny, F. and Zernicka-Goetz, M. (2000) *Nature Cell Biol.* 2, 70-75.
39. Yang, D., Lu, H., and Erickson, J. W. (2000) *Current Biology* 10, 1191-1200.
40. Zamore, P. D., Tuschl, T., Sharp, P. A., and Bartel, D. P. (2000) *Cell* 101, 25-33.
41. U.S. Pat. No. 4,683,195 issued to Mullis et. al.
42. U.S. Pat. No. 4,683,202 issued to Mullis et. al.
43. U.S. Pat. No. 4,965,188 issued to Mullis et. al.
44. U.S. Pat. No. 5,075,216 issued to Innis et. al.
45. U.S. Pat. No. 5,322,770 issued to Gelfand et. al.
46. U.S. Pat. No. 5,817,465 issued to Mallet et. al.
47. U.S. Pat. No. 5,888,779 issued to Kacian et. al.
48. U.S. Pat. No. 6,197,554 issued to Shi-Lung Lin et. al.
49. U.S. Pat. No. 6,130,040 issued to Shi-Lung Lin et. al.
50. U.S. Pat. No. 5,795,715 issued to Livache et. al.
51. Patent Cooperation Treaty Publication No. WO 00/75356 issued to Lin et. al.
52. U.S. Pat. No. 4,289,850 issued to Robinson.
53. U.S. Pat. No. 6,159,714 issued to Lau.
54. U.S. Pat. Nos. 4,945,082, 4,950652, 5,091,374 and 5,906, 980 issued to Carter.

It is understood that the examples and embodiments described herein are for illustrative purposes only and that various modifications or changes in light thereof will be suggested to persons skilled in the art, and are to be included within the spirit and purview of the invention as set forth in the appended claims. All publications and patents cited herein are incorporated herein by reference in their entirety for all purposes.

What is claimed is:

1. A nucleic acid molecule comprising:
a hybridized RNA-DNA duplex of at least 500 base pairs
wherein the RNA of the RNA-DNA duplex is a ribonucleic acid molecule comprising a sequence substantially complementary to a targeted RNA sequence;
wherein the DNA of the RNA-DNA duplex is a deoxyribonucleic acid molecule comprising a sequence substantially complementary to the RNA of the RNA-DNA duplex; and
wherein targeted RNA sequence is necessary for expression of a targeted gene selected from the group consisting of a functional gene, a pathogenic nucleic acid, a viral gene/genome, a bacterial gene, a mutate gene, and an oncogene.

2. The nucleic acid molecule according to claim 1,
wherein the targeted RNA sequence comprises a ribonucleotide sequence completely or partially complementary to the nucleic acid molecule.

3. The nucleic acid molecule according to claim 1,
wherein the targeted RNA is mRNA.

4. The composition according to claim 1,
wherein the RNA molecule is a sense RNA molecule that is homologous to an mRNA sequence of a targeted gene, and
wherein the DNA molecule is an antisense DNA molecule that is complementary to the targeted mRNA.

5. The nucleic acid molecule according to claim 1,
wherein the RNA molecule is an antisense RNA molecule that is partially complementary to a specific messenger RNA (mRNA) sequence to be targeted in the cell, and
wherein the DNA molecule is a sense DNA molecule, which is in the same orientation and contains homologous sequence composition as the targeted mRNA.

6. The nucleic acid molecule according to claim 1,
wherein the DNA of the RNA-DNA hybrid further comprises a weak binding nucleotide analog.

7. The nucleic acid molecule according to claim 6,
wherein the weak binding nucleotide analog is selected from the group consisting of ribonucleotide in DNA linkage, uridine (U), inosine (I), xanthine (X), hypoxanthine (HX) and their derivative analogs, wherein said derivative analog is one selected from hexose-containing, 2'-5' linked, phosphothio-linked, mehtylthio-linked, morpholino-linked and peptide-linked nucleotide analogs.

8. The nucleic acid molecule according to claim 6,
wherein the DNA of the RNA-DNA hybrid further comprises inosine or derivatives thereof.

9. The nucleic acid molecule of claim 1, wherein the targeted gene is an oncogene selected from the group consisting of β-catenin, bcl-2, c-myc.

10. The nucleic acid molecule of claim 9, wherein the oncogene is β-catenin.

11. The nucleic acid molecule of claim 9, wherein the oncogene is c-myc.

12. The nucleic acid molecule of claim 1,
wherein the targeted gene is a viral gene/genome, and the virus is HIV.

13. The nucleic acid molecule of claim 12,
wherein the targeted gene encodes a transcript of viral gag-pro-pol proteins.

* * * * *

SEQUENCE LISTING

<160> NUMBER OF SEQ ID NOS: 19

<210> SEQ ID NO 1
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 1
ccagtgaatt gtaatacgac tcactatagg gaattttttt tttttttttt tttttt     57

<210> SEQ ID NO 2
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 2
cccccccccc cc     12

<210> SEQ ID NO 3
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 3
ccagtgaatt gtaatacgac tcactatagg gaaccccccc cccg     44

<210> SEQ ID NO 4
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 4
ccagtgaatt gtaatacgac tcactatagg gaaccccccc ccca     44

<210> SEQ ID NO 5
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 5
ccagtgaatt gtaatacgac tcactatagg gaaccccccc ccct     44

<210> SEQ ID NO 6
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 6
tttttttttt tttttttttt tttt     24

<210> SEQ ID NO 7
<211> LENGTH: 25
<212> TYPE: DNA

```
<213> ORGANISM: Artificial Sequence
<220> FEATURE:
<223> OTHER INFORMATION: Synthetic oligonucleotide

<400> SEQUENCE: 7
atttctcttg gtgggcttca tctgc                                           25

<210> SEQ ID NO 8
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 8
ccagtgaatt gtaatacgac tcactatagg cgctcataga cacgttggcc aggcttc       57

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
atggcaatca agaaagtaag c                                               21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gtacaacaac tgcacaaata g                                               21

<210> SEQ ID NO 11
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 11
aaacgacggc cagtgaattg taatacgact cactataggc ggatgactga gtacctgaac    60
cggc                                                                  64

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12
cttcttcagg ccagggaggc atgg                                            24

<210> SEQ ID NO 13
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 13
```

```
aaacgacggc cagtgaattg taatacgact cactataggc cttcttcagg ccagggaggc    60
atgg                                                                 64
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
ggatgactga gtacctgaac cggc                                           24
```

```
<210> SEQ ID NO 15
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 15
aaacgacggc cagtgaattg taatacgact cactataggc gctctgaaga cagtctgtcg    60
tgatgg                                                               66
```

```
<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
atggcaaccc aagctgactt gatc                                           24
```

```
<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: I
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
```

```
<223> OTHER INFORMATION: n is a, c, g, or t

<400> SEQUENCE: 17
ggatgncngn cnccttgttg gtcc                                           24

<210> SEQ ID NO 18
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 18
gtgctcaggc aacttcatgg gtttcaactg cggaaactgt aagtttggat ttggggccc     60 aaattgtaca gagaagcgag                                                80

<210> SEQ ID NO 19
<211> LENGTH: 37
<212> TYPE: RNA
<213> ORGANISM: Artificial Sequence
<220> FEATURE:
<223> OTHER INFORMATION: Synthetic oligonucleotide

<400> SEQUENCE: 19
cucgcuucuc uguacaauuu gggcccccaa auccaaa                             37
```